United States Patent
Pahan

(10) Patent No.: US 11,351,142 B2
(45) Date of Patent: Jun. 7, 2022

(54) COMPOSITION AND METHOD FOR TREATING NEURONAL CEROID LIPOFUSCINOSIS

(71) Applicant: Rush University Medical Center, Chicago, IL (US)

(72) Inventor: Kalipada Pahan, Skokie, IL (US)

(73) Assignee: Rush University Medical Center, Chicago, IL (US)

(*) Notice: Subject to any disclaimer, the term of this patent is extended or adjusted under 35 U.S.C. 154(b) by 150 days.

(21) Appl. No.: 16/515,836

(22) Filed: Jul. 18, 2019

(65) Prior Publication Data

US 2019/0336465 A1 Nov. 7, 2019

Related U.S. Application Data

(60) Continuation of application No. 15/663,512, filed on Jul. 28, 2017, now Pat. No. 10,357,471, which is a division of application No. 14/649,069, filed as application No. PCT/US2013/073606 on Dec. 6, 2013, now Pat. No. 9,750,712.

(60) Provisional application No. 61/734,679, filed on Dec. 7, 2012.

(51) Int. Cl.
 *A61K 31/216* (2006.01)
 *A61K 31/192* (2006.01)
 *A61K 31/203* (2006.01)

(52) U.S. Cl.
 CPC .......... *A61K 31/216* (2013.01); *A61K 31/192* (2013.01); *A61K 31/203* (2013.01)

(58) Field of Classification Search
 None
 See application file for complete search history.

(56) References Cited

U.S. PATENT DOCUMENTS

| 2002/0055529 A1 | 5/2002 | Bisgaier |
| 2008/0009516 A1 | 1/2008 | Wustman |
| 2013/0023488 A1 | 1/2013 | Wu |

OTHER PUBLICATIONS

Choi et al. "Treatment of hyperlipidemia associated with Niemann-Pick disease type B by fenofibrate," Eur J Pediatr (2006) 165: 138-139. (Year: 2006).*
Choi, Jin-Ho et al.; "Treatment of hyperlipidemia associated with Niemann-Pick disease type B by fenofibrate" European Journal of Pediatrics, vol. 165, No. 2; Feb. 1, 2006; pp. 138-139.
Dheen, Thameem S.; "Retinoic Acid Inhibits Expression of TNF-a and iNOS in Activated Rat Microglia"; GLIA, vol. 50, No. 1; XP002440434; Apr. 1, 2005; pp. 21-31.
Ghosh, Arunava et al.; Gemifibrozil and Fenofibrate, Food and Drug Administration-approved Lipid-lowering Drugs, Up-regulate Tripeptidyl-peptidase 1 in Brain Cells via Peroxisome Proliferator-activated Receptor a: Implications for Late Infantile Batten Disease Therapy; Journal of Biological Chemistry, vol. 287, No. 46 XP055099483; Sep. 18, 2012; pp. 38922-38935.
Kreisler, Alexandre et al.; "Lipid-lowering drugs in the MPTP mouse model of Parkinson's disease: Fenofibrate has a neuroprotective effect, whereas bezafibrate and HMG-CoA reductase inhibitors do not"; Brain Research, vol. 1135 XP026864901 Mar. 2, 2007; pp. 77-84.
International Search Report dated Jan. 30, 2014 for International Application No. PCT/US2013/073606.
Birch et al. "Retinal Degeneration in Retinitis Pigmentosa and Neuronal Ceroid Lipofuscinosis: An Overview," Molecular Genetics and Metabolism 66, 356-366 (1999) (Year: 1999).
Berson et al. "A randomized trial of vitamin A and vitamin E supplementation for retinitis pigmentosa," Arch Ophthalmol. Jun. 1993; 111(6):Abstract. (Year: 1993).

* cited by examiner

*Primary Examiner* — Jeffrey S Lundgren
*Assistant Examiner* — Michael J Schmitt
(74) *Attorney, Agent, or Firm* — Taft Stettinius & Hollister LLP; Joseph M. Bennett-Paris

(57) ABSTRACT

Provided herein are methods for treatment of a neurodegenerative disease, such as neuronal ceroid lipofuscinosis including administering to a subject in need of such treatment a composition comprising a therapeutically effective amount of an agent that mediates upregulation of TPP1.

8 Claims, 21 Drawing Sheets

Specification includes a Sequence Listing.

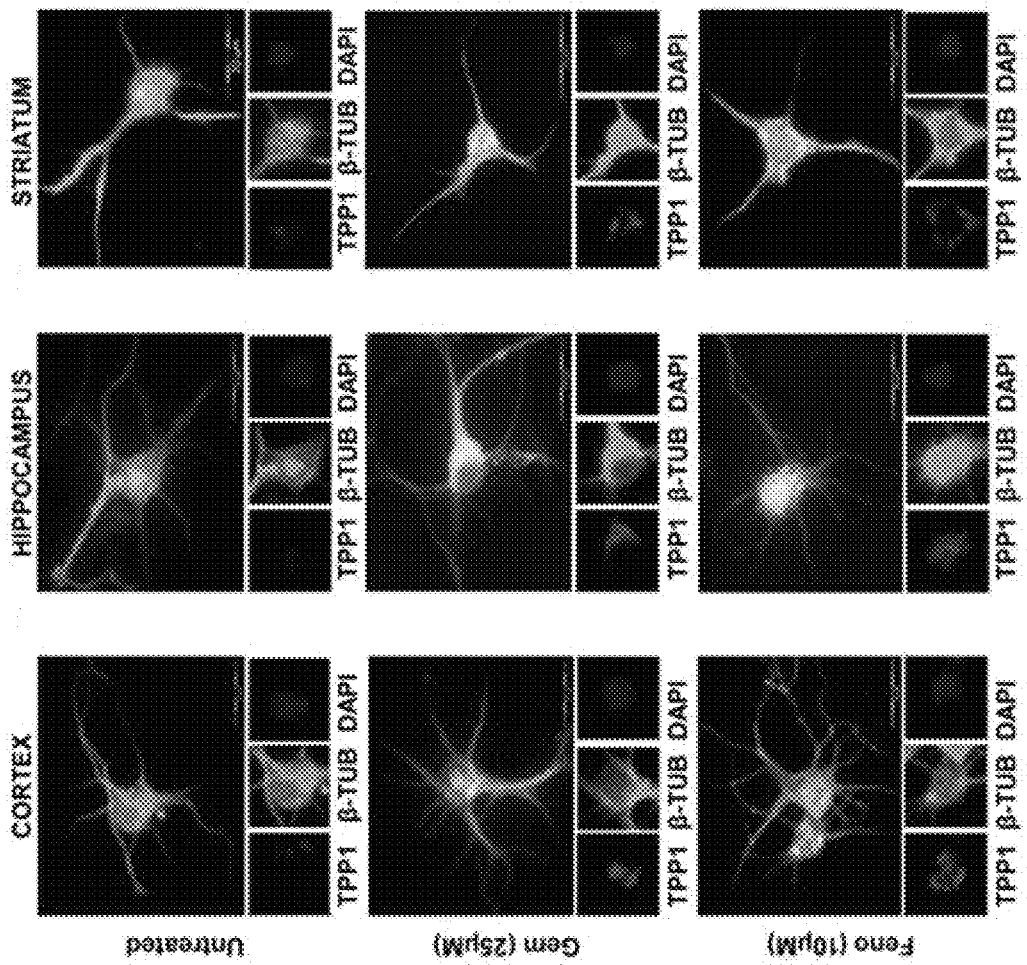

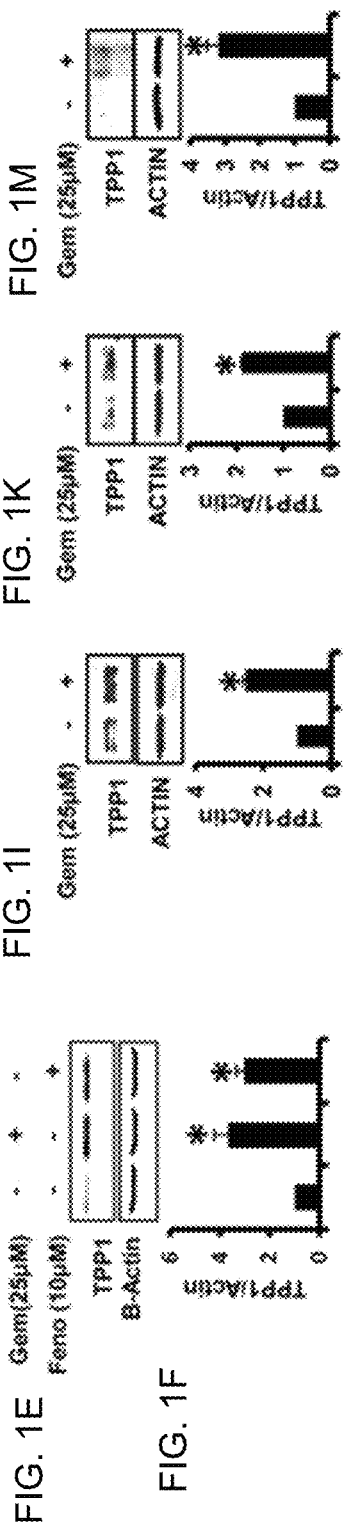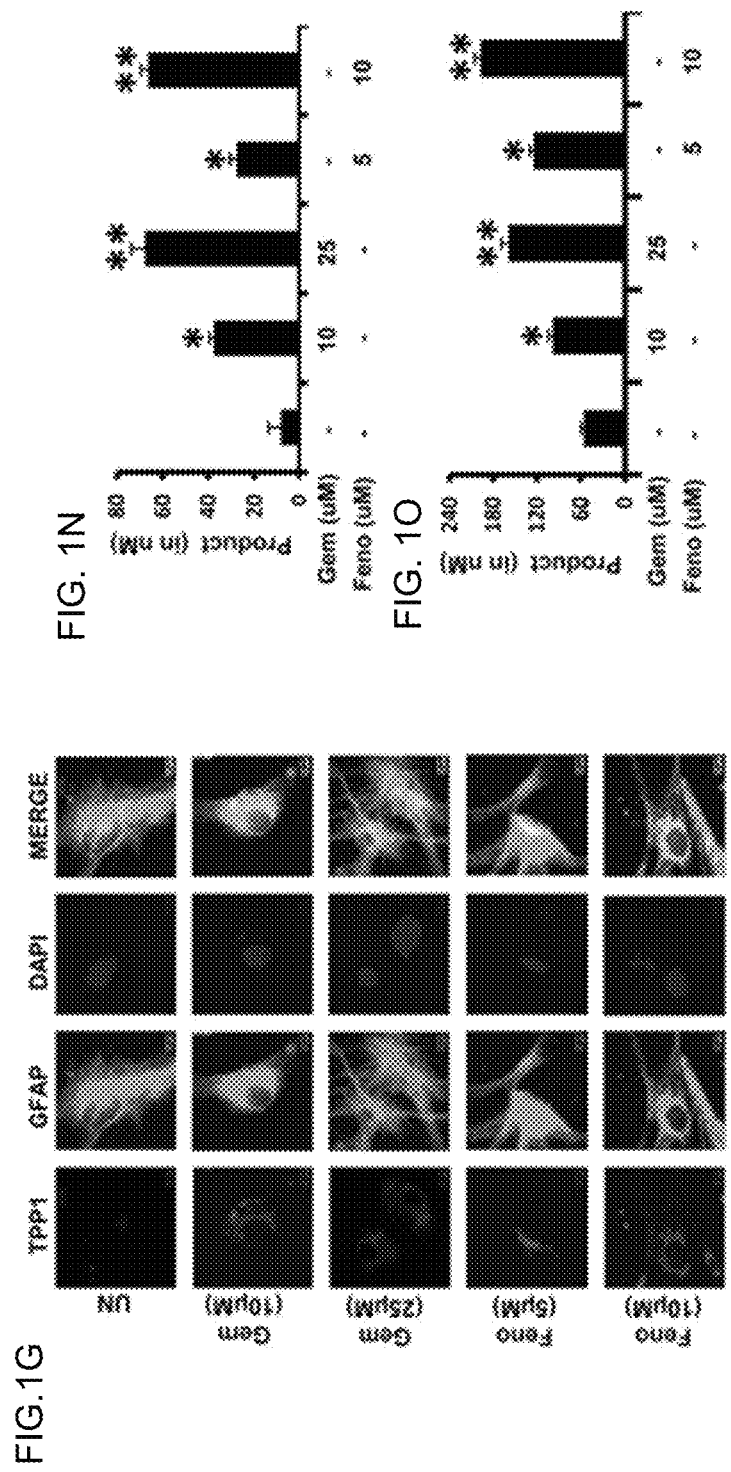

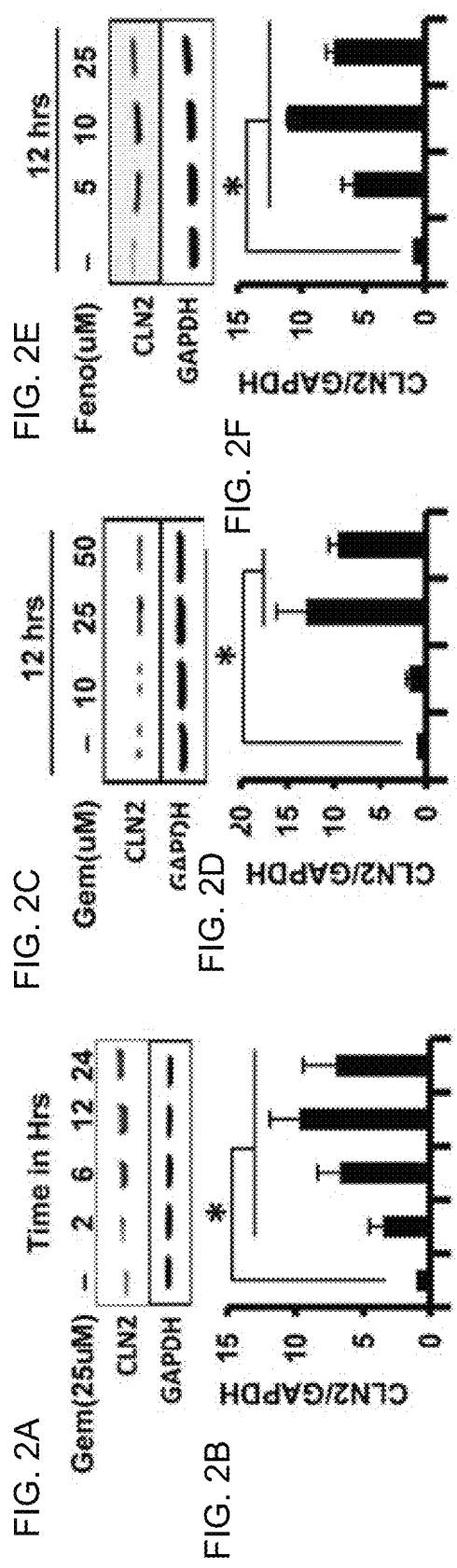
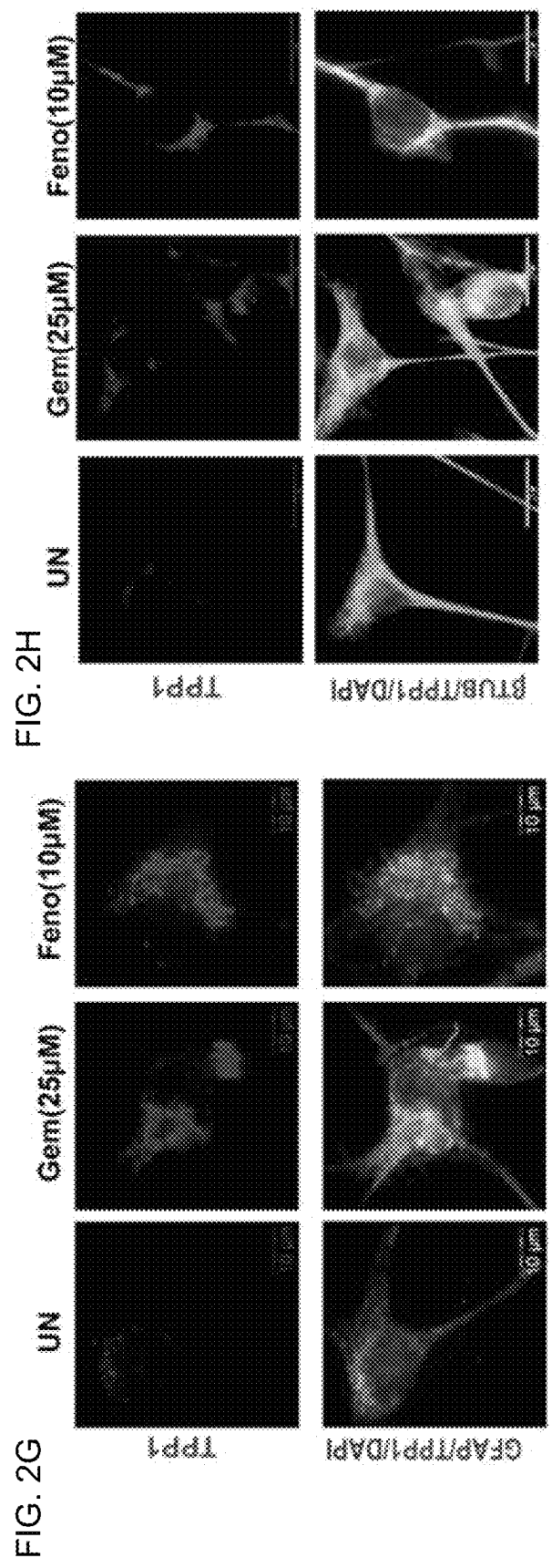

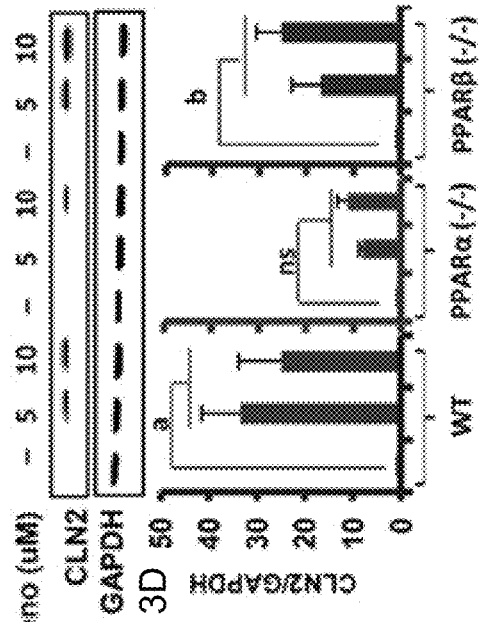
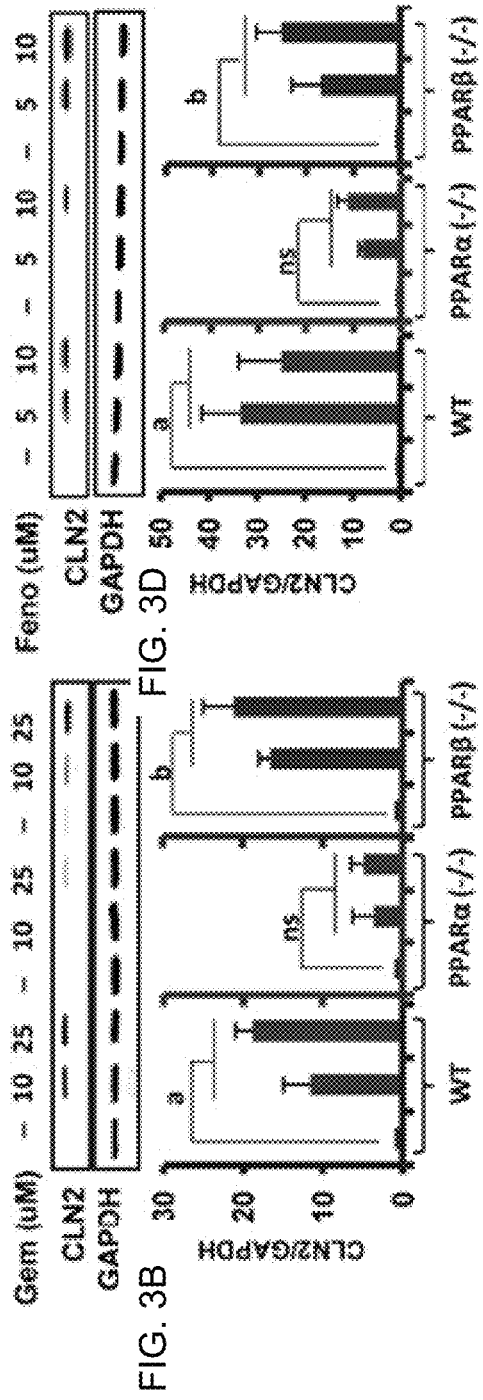
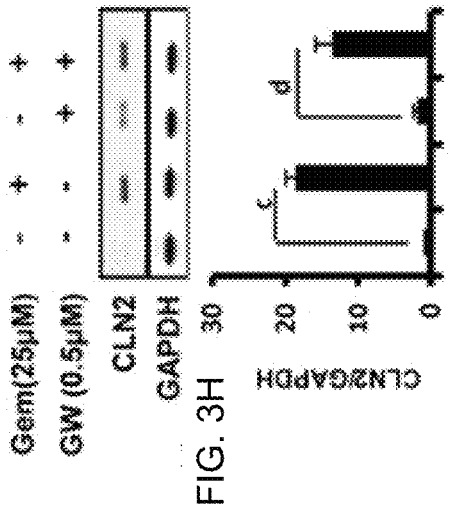
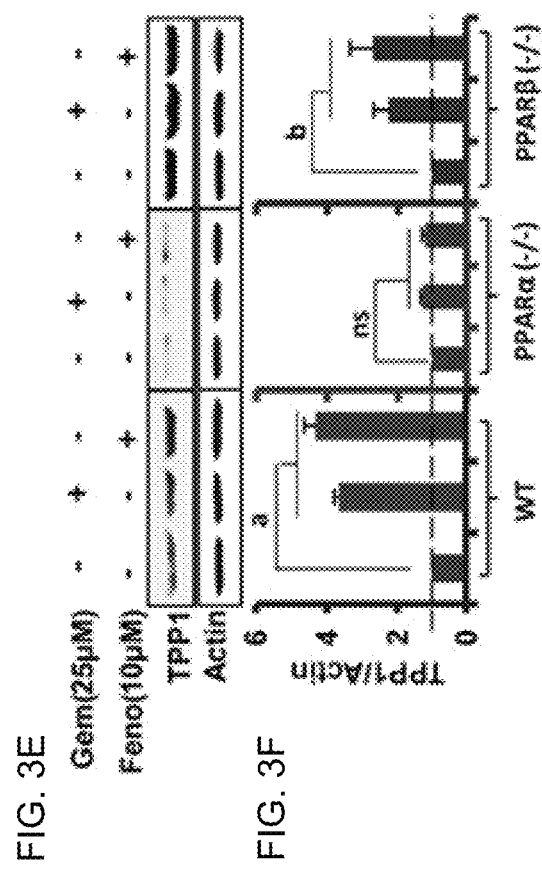
FIG. 3A  FIG. 3B  FIG. 3C  FIG. 3D  FIG. 3E  FIG. 3F  FIG. 3G  FIG. 3H

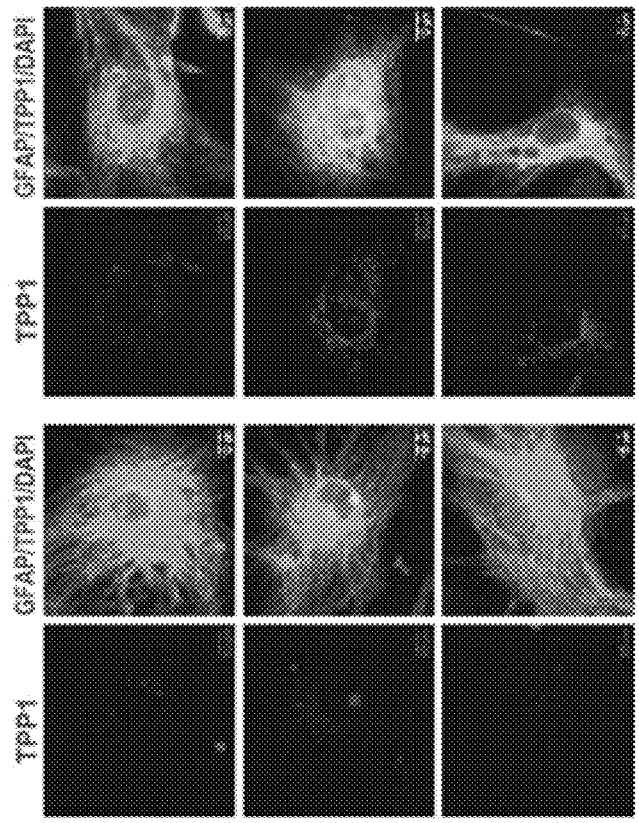
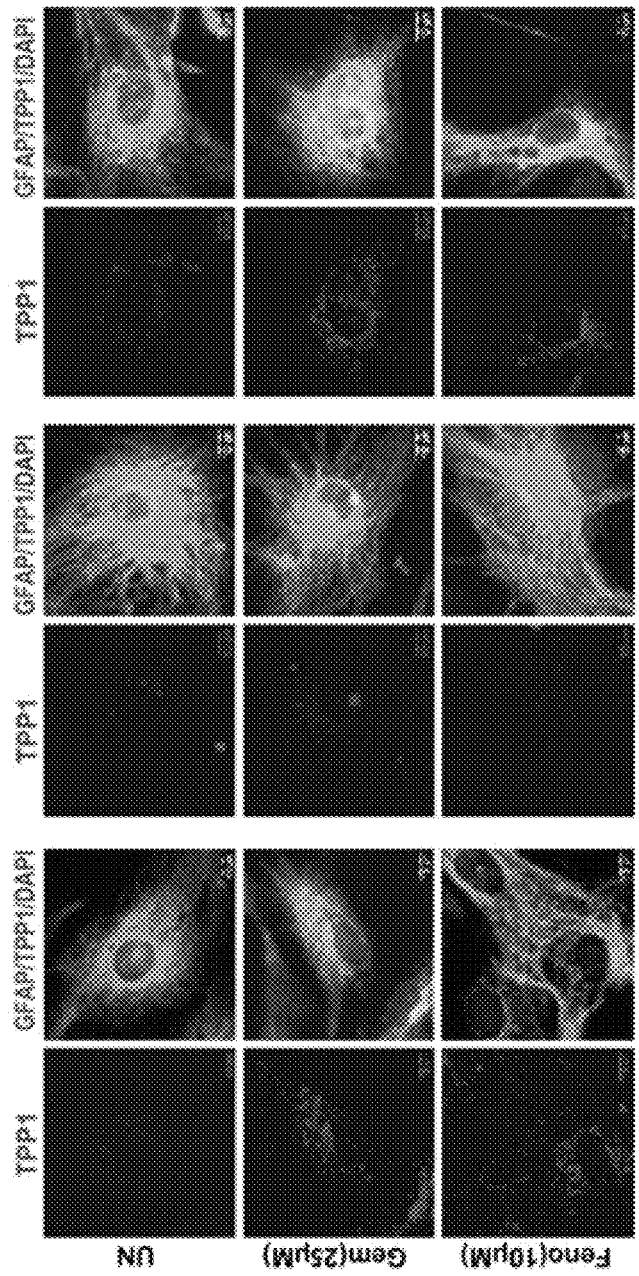
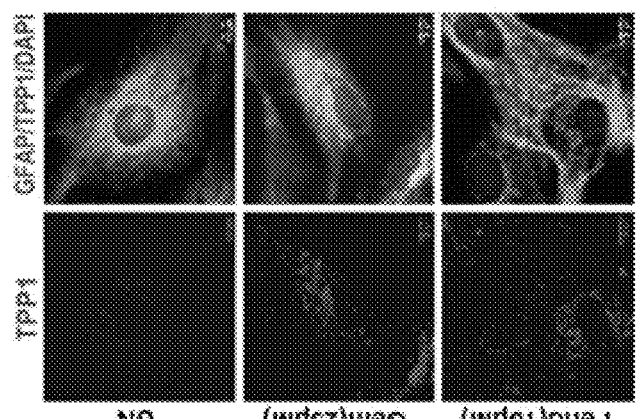
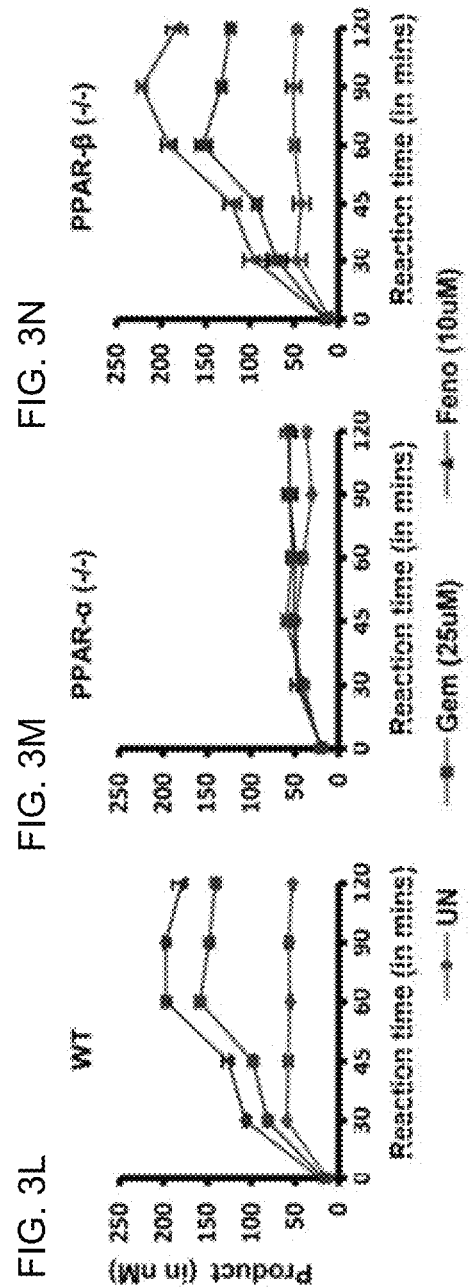
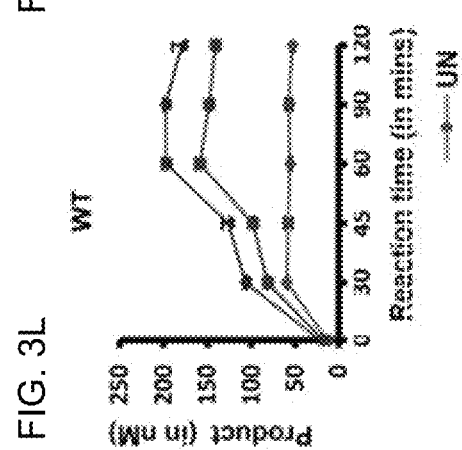

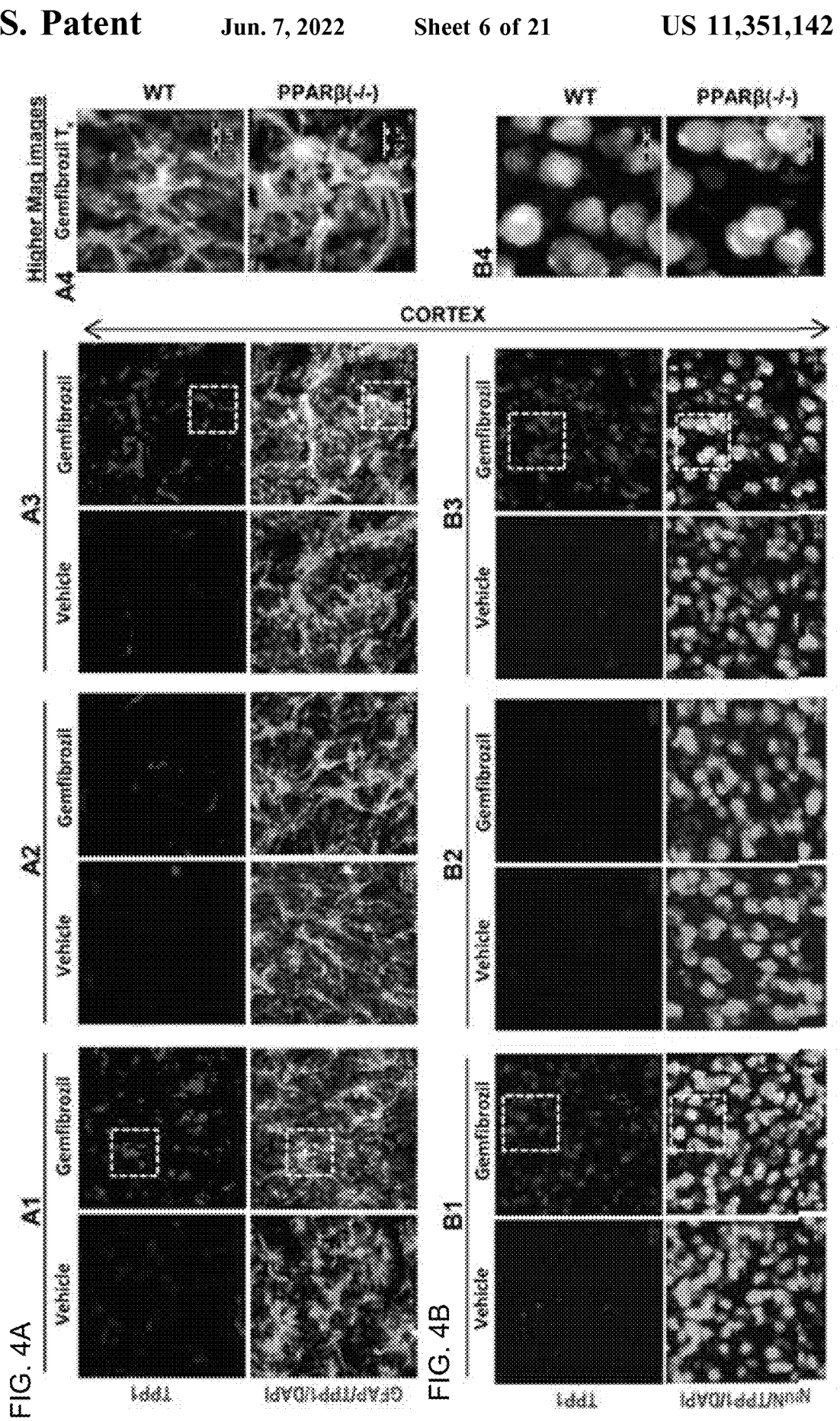

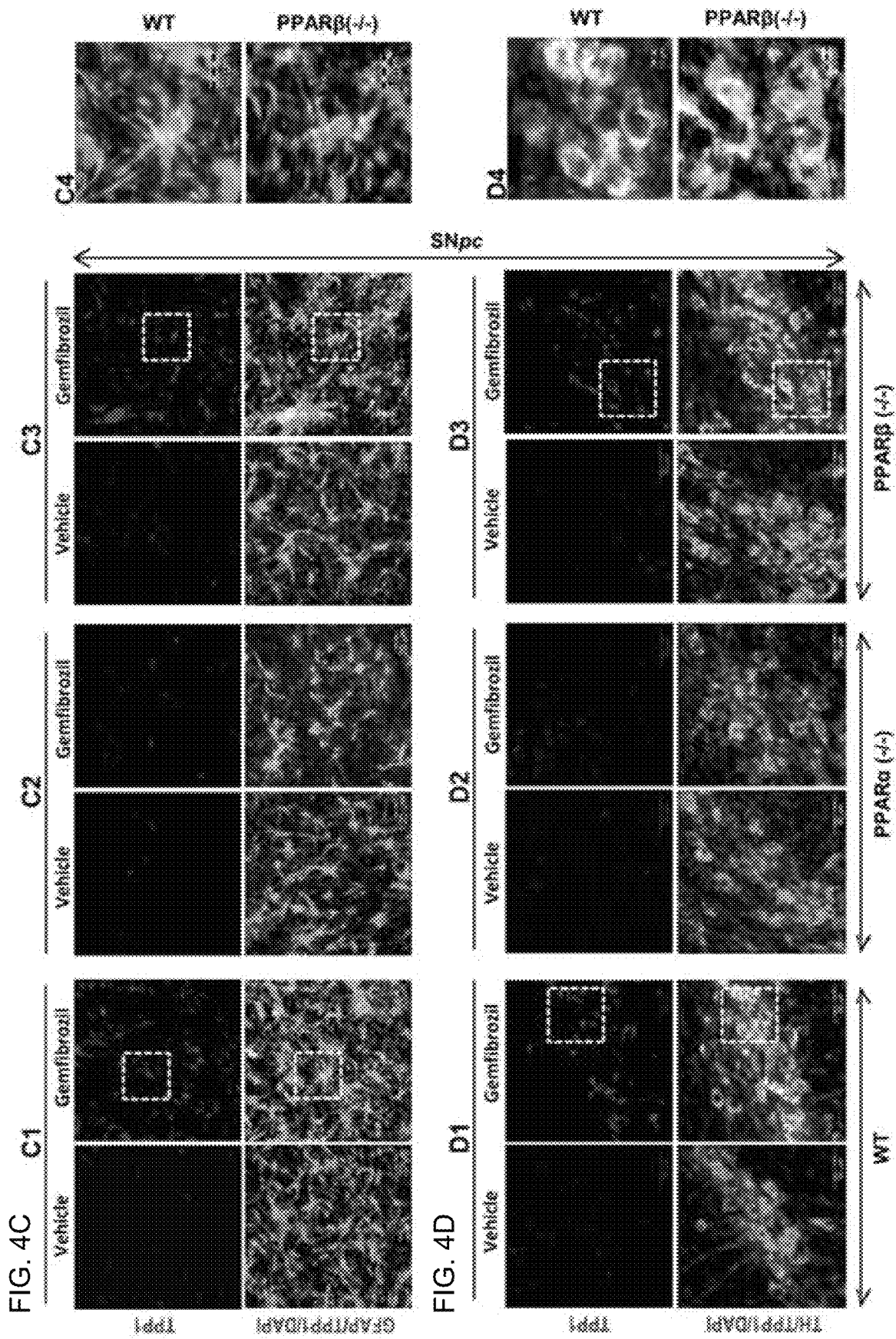

FIG. 5A
FIG. 5B
FIG. 5C
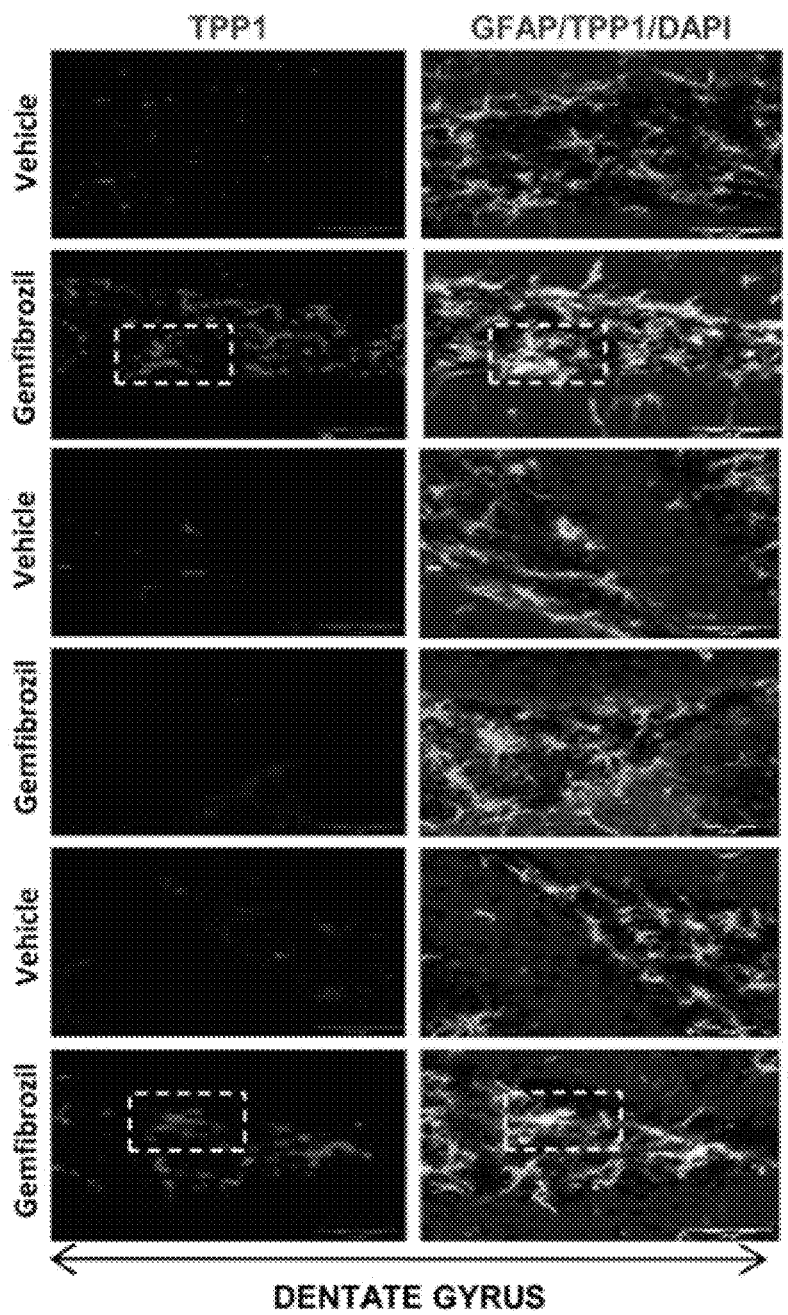
FIG. 5D
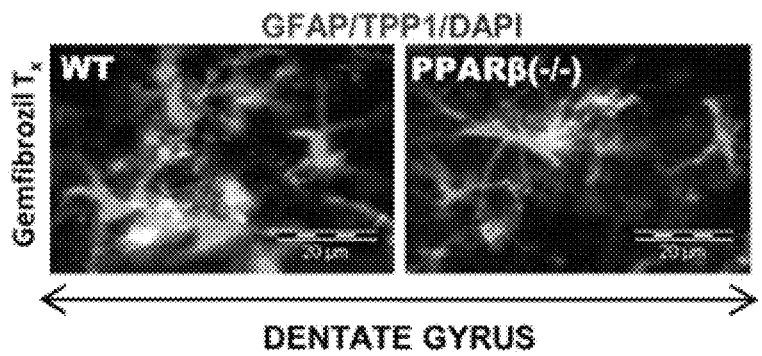

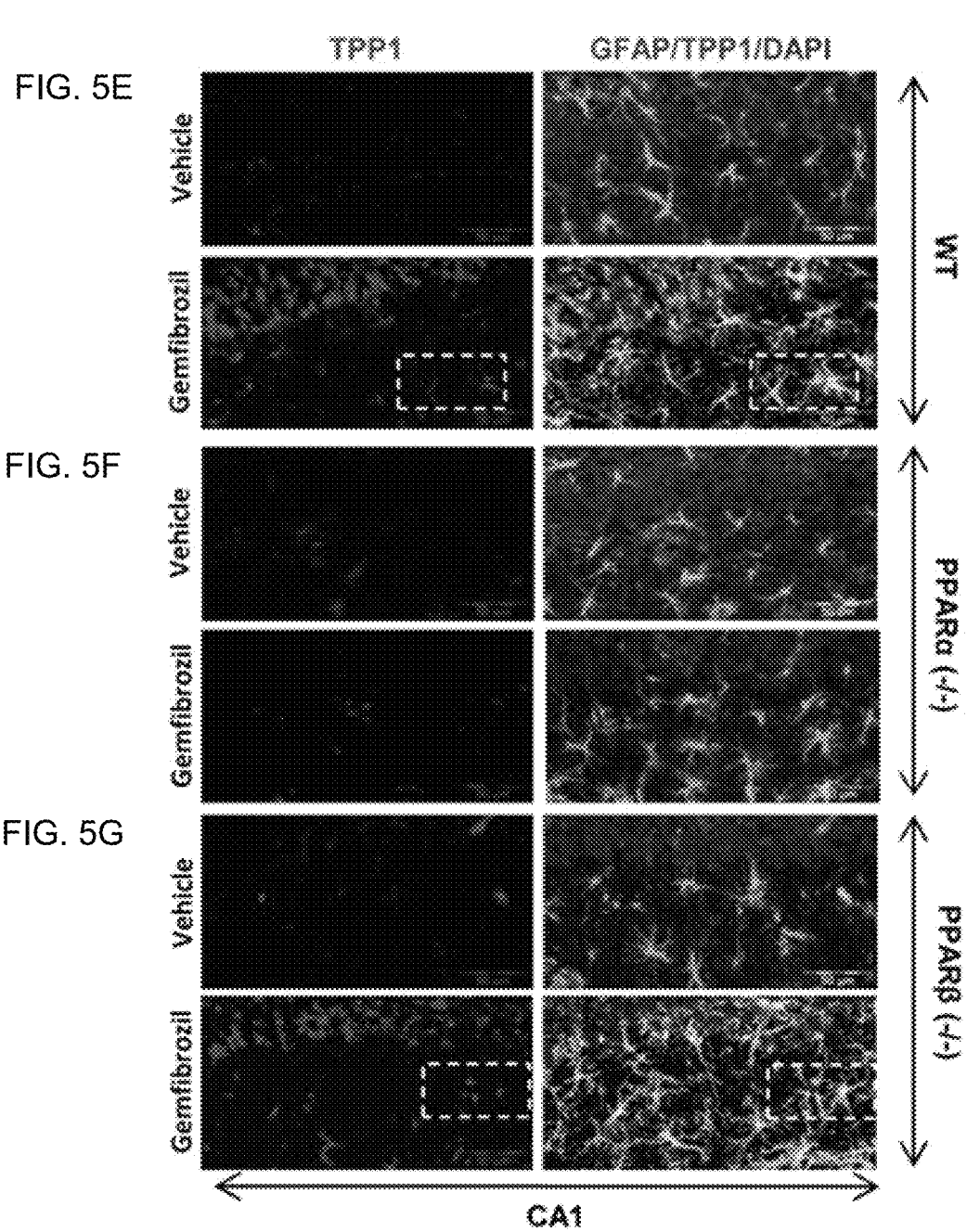
FIG. 5E
FIG. 5F
FIG. 5G
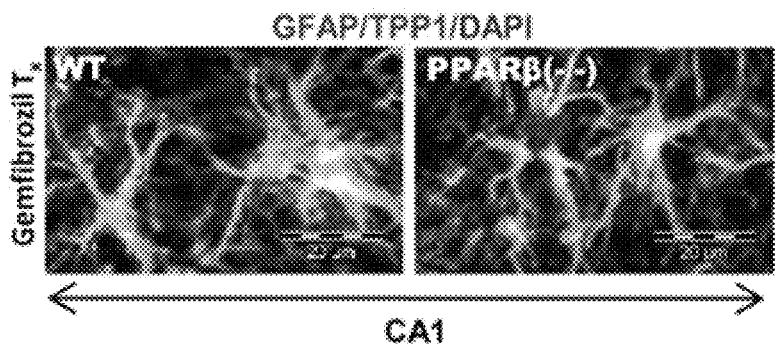
FIG. 5H

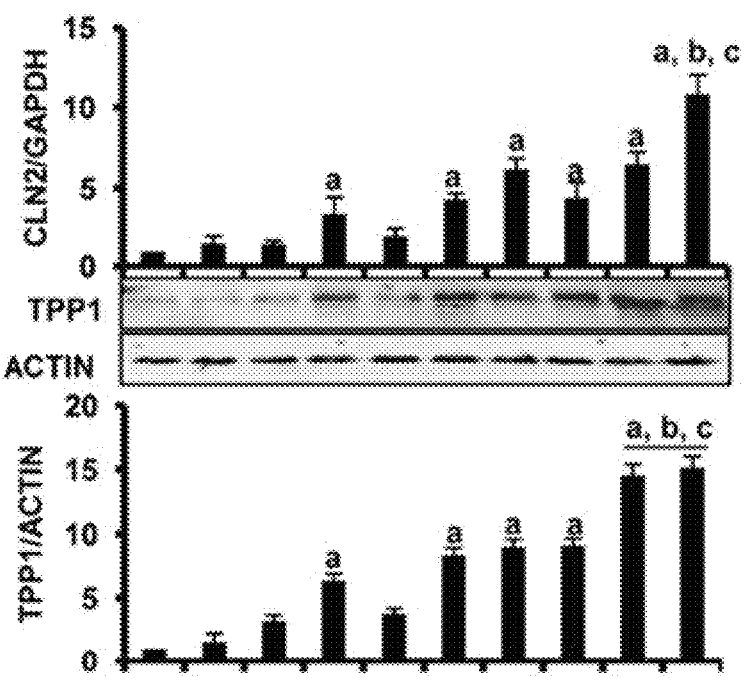

FIG. 13A
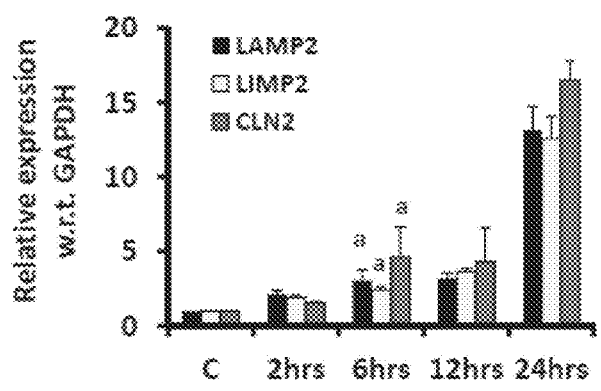
FIG. 13B
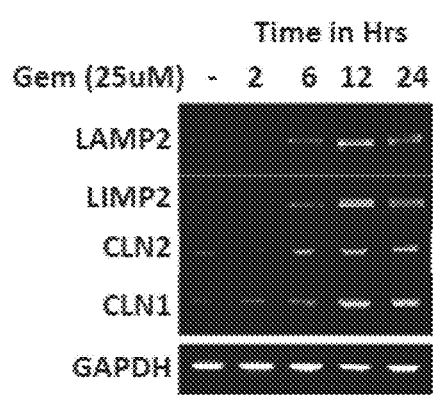
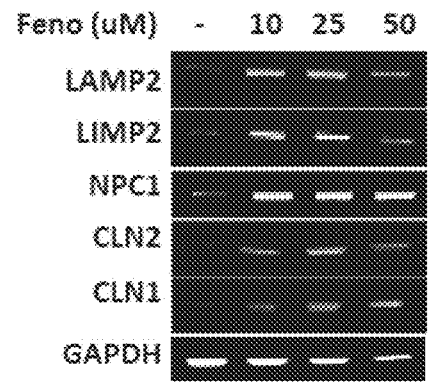
FIG. 13C

COMPOSITION AND METHOD FOR TREATING NEURONAL CEROID LIPOFUSCINOSIS

RELATED APPLICATIONS

This application is a continuation application of U.S. application Ser. No. 15/663,512, filed Jul. 28, 2017, which is divisional application of U.S. application Ser. No. 14/649,069, filed Jun. 2, 2015, which claims the benefit under 35 U.S.C. § 371 of International Application No. PCT/US2013/073606, filed Dec. 6, 2013, which claims the benefit of U.S. Provisional Application No. 61/734,679 filed Dec. 7, 2012, which are incorporated by reference herein their entirety.

SUPPORT

This invention was made with government support under contract numbers AT6681, NS64564 and NS71479 awarded by the National Institutes of Health. The government has certain rights in the invention.

TECHNICAL FIELD

The present invention relates to a composition and method for treating a neurodegenerative disease, such as neuronal ceroid lipofuscinosis.

BACKGROUND

Neuronal ceroid lipofuscinosis (NCL) is a group of neurodegenerative diseases mainly composed of typical autosomal recessive lysosomal storage disorders. The NCLs can be characterized by clinical manifestations like progressive mental deterioration, cognitive impairment, visual failures, seizures and deteriorating motor function accompanied by histological findings such as the accumulation of autofluorescent storage material in neurons or other cell types (1). The NCLs have been subdivided into several groups (Type1-10) based on the age of onset, ultrastructural variations in accumulated storage materials, and genetic alterations unique to each specific disease type (2,3).

Late infantile neuronal ceroid lipofuscinosis (Jansky-Bielschowsky disease, LINCL, Type 2) typically produces symptoms at the age of 2-4 years, progresses rapidly and ends in death between ages 8 to 15 as a result of a dramatic decrease in the number of neurons and other cells (2,4). LINCL is associated with mutations in the Cln2 gene, a 13 exon and 12 intron gene of total length of 6.65 kb mapped to chromosome 11p15.5. The Cln2 gene encodes lysosomal tripeptidyl tripeptidase I (TPP-I or pepstin insensitive protease), a 46 KD protein that function in the acidic environment of the lysosomal compartment to remove tripeptides from the amino terminus of proteins (5,6). This mutation in the Cln2 gene results in a deficiency and/or loss of function of the TPP1 protein that leads to intralysosomal accumulation of autofluoroscent lipopigments known as ceroid-lipofuscin (5). Currently there is no established treatment or drugs available for this disease; all approaches are merely supportive or symptomatic, indicating a need for novel therapeutic approaches (7). However, there are different variants of Cln2 mutations and there have been reports that residual TPP-I activity can be found in patients with LINCL, indicating that there must be a few copies of normal Cln2 gene remaining in patients affected with LINCL (8,9).

SUMMARY

Provided herein is a method for treatment of a neurodegenerative disease. The neurodegenerative disease may be neuronal ceroid lipofuscinosis, Alzheimer's disease, Huntington's disease, Amyotrophic lateral sclerosis (ALS), Parkinson's disease, including Parkinson's plus diseases such as multiple system atrophy (MSA), progressive supranuclear palsy (PSP), corticobasal degeneration (CBD) or dementia with Lewy bodies (DLB). The neurodegenerative disorder may be characterized by defective autophage. Such disorders include Alzheimer's, Parkinson's disease, and Huntington's disease. The neurodegenerative disease may be a lysosomal storage disorder. The lysosomal storage disorder may be, for example, Tay-Sach's disease, Fabry disease, Niemann-Pick disease, Gaucher disease, Hunter Syndrome, Alpha-mannosidosis, Aspartylglucosaminuria, Cholesteryl ester storage disease, Chronic Hexosaminidase A Deficiency, Cystinosis, Danon disease, Farber disease, Fucosidosis, or Galactosialidosis.

The method may comprise administering to a subject in need of such treatment a composition comprising a therapeutically effective amount of an agent that mediates upregulation of TPP1. The agent may be a lipid-lowering drug. The lipid-lowering drug may be a fibrate. The fibrate may be gemfibrozil or fenofibrate. The neuronal ceroid lipofuscinosis may be late infantile neuronal ceroid lipofuscinosis or Batten disease. TPP1 may be upregulated by increasing TPP1 mRNA levels, increasing TPP1 protein levels, increasing TPP1 enzymatic activity, or activating a PPARα-RXRα heterodimer.

The composition may further comprise a therapeutically effective amount of all-trans retinoic acid. The agent may be a fibrate. Administering all-trans retinoic acid and the fibrate may provide a greater therapeutic effect in the subject than administration of all-trans retinoic acid or the fibrate alone.

Also provided herein is a method for treatment of neuronal ceroid lipofuscinosis, comprising administering to a subject in need of such treatment a composition comprising a therapeutically effective amount of an agent, wherein the agent restores TPP1 activity. The agent may be a fibrate. The fibrate may be gemfibrozil or fenofibrate. The therapeutically effective amount of the fibrate may be lower when the fibrate is administered in combination with all-trans retinoic acid.

Further provided herein is a method for treatment of neuronal ceroid lipofuscinosis, comprising administering to a subject in need of such treatment a composition comprising a therapeutically effective amount of an agent that mediates upregulation of a gene selected from the group of Cln1, Cln2, Cln3, and any combination thereof. The agent may be a fibrate. The fibrate may be gemfibrozil or fenofibrate.

BRIEF DESCRIPTION OF THE DRAWINGS

FIGS. 1A-1O show gemfibrozil and fenofibrate upregulating TPP1 mRNA and functionally active protein in mouse brain cells. (FIGS. 1A, 1B) Mouse primary astrocytes were treated with 25 µM gemfibrozil in serum-free DMEM/F12 for 2, 6, 12, and 24 hrs followed by monitoring the mRNA expression of Cln1, Cln2 and Cln3 by semi-quantitative RT-PCR (FIG. 1A) and qPCR (FIG. 1B) (for Cln2). (FIG. 1C, 1D) Mouse astrocytes were treated with different concentrations of gemfibrozil for 24 hrs under the same culture conditions followed by monitoring the mRNA expression of Cln2 by semi-quantitative RT-PCR (FIG. 1C) and real-time PCR (FIG. 1D). (FIG. 1E) Mouse primary astrocytes were treated with 25 µM gemfibrozil and 10 µM fenofibrate for 24 hrs under the same culture conditions followed by Western blot for TPP1. (FIG. 1F) Densitometric analysis of TPP1 expression (relative to β-Actin) by gemfibrozil and fenofibrate treatment. (G) Mouse primary astrocytes were treated with different concentrations of gemfibrozil and fenofibrate under similar culture conditions and were double-labeled for TPP1 (red) and GFAP (green). Scale bar=10 µM. (FIGS. 1H, 1J, 1L) Mouse primary neurons were isolated from different parts of the brain and were treated with 25 µM gemfibrozil and 10 µM fenofibrate in neurobasal media containing B27-AO for 24 hrs and were double-labeled for TPP1 (red) and β-tubulin (green) (H—for cortical neurons, J—for hippocampal neurons, L—for striatal neurons). DAPI was used to stain nuclei. Scale bar=20 µM. (FIGS. 1I, 1K, 1M) Mouse neurons were treated with 25 µM gemfibrozil under same culture conditions for 24 hrs followed by Western blot for TPP 1 (I—for cortical neurons, K—for hippocampal neurons, M—for striatal neurons). Graphs represent the densitometric analysis of TPP1 level (relative to β-Actin). (FIG. 1N) Mouse primary neurons were treated with different concentrations of gemfibrozil and fenofibrate in B27-AO containing Neurobasal media for 24 hrs followed by the activity assay using cell extract containing 5 g of total protein. (FIG. 1O) Mouse primary astrocytes were treated with different concentrations of gemfibrozil and fenofibrate in serum free DMEM/F12 medium for 24 hrs followed by the activity assay using cell extract containing 5 g of total protein. All results are mean±SEM of at least three independent experiments. $p^*<0.05$ vs control; $p^{**}<0.01$ vs control.

FIGS. 2A-2H show gemfibrozil and fenofibrate upregulating TPP1 mRNA and protein in human primary astrocytes and SHSY5Y neuronal cells. (FIGS. 2A, 2B) Human primary astrocytes were treated with 25 µM gemfibrozil in serum-free DMEM/F12 for 2, 6, 12 and 24 hrs followed by monitoring the mRNA expression of Cln2 by semi-quantitative RT-PCR (FIG. 2A) and real-time PCR (FIG. 2B). (FIGS. 2C-2F) Human primary astrocytes were treated with different concentrations of gemfibrozil and fenofibrate for 12 hrs under the same culture conditions followed by monitoring the mRNA expression of Cln2 by semi-quantitative RT-PCR (FIG. 2C—for gemfibrozil, FIG. 2E—for fenofibrate) and real-time PCR (FIG. 2D—for gemfibrozil, F—for fenofibrate). (FIG. 2G) Human primary astrocytes were treated with 25 µM of gemfibrozil and 10 µM fenofibrate for 24 hrs under similar culture conditions and were double-labeled for TPP1 (red) and GFAP (green). (FIG. 2H) SH-SY5Y cells were treated with 25 µM of gemfibrozil and 10 µM fenofibrate in B27-AO containing Neurobasal media for 24 hrs and were double-labeled for TPP1 (red) and β-tubulin (green). DAPI was used to stain nuclei. All results are mean±SEM of at least three independent experiments. $p^*<0.05$ vs control. UN-Untreated. Scale bar=10 µM.

FIGS. 3A-3N show involvement of PPARα in fibrate drug-mediated upregulation of TPP1 mRNA and protein. (FIGS. 3A-3E) Mouse primary astrocytes isolated from PPARα$^{-/-}$ and PPARβ$^{-/-}$ and wild type mouse were treated with different concentrations of gemfibrozil and fenofibrate in serum free DMEM/F12 for 24 hrs followed by monitoring the mRNA expression of Cln2 by semi-quantitative RT-PCR (FIGS. 3A, 3C) and real-time PCR (FIGS. 3B, 3D) and protein level of TPP1 by Western blot (FIG. 3E). (FIG. 3F) Densitometric analysis of TPP1 levels (relative to 3-Actin) in PPARα$^{-/-}$ and PPARβ$^{-/-}$ and wild type astrocytes by gemfibrozil and fenofibrate treatment. $p^a<0.05$ vs WT control; $p^b<0.05$ vs PPARβ$^{-/-}$ control; ns—not significant w.r.t PPARα$^{-/-}$ control (FIGS. 3G, 3H) Mouse primary astrocytes isolated from WT mice were pre-treated with GW9662 for 30 min followed by treatment with 25 µM gemfibrozil under similar culture conditions. The mRNA expression of Cln2 was monitored by semi-quantitative RT-PCR (FIG. 3G) real time PCR (FIG. 3H). $p^c<0.05$ vs control; $p^d<0.05$ vs only GW treated. (FIGS. 3I-3K) Mouse primary astrocytes isolated from PPARα$^{-/-}$ and PPARβ$^{-/-}$ and WT mice were treated with 25 µM gemfibrozil and 10 µM fenofibrate in serum free DMEM/F12 for 24 hrs and double-labeled for TPP (red) and GFAP (green) (FIG. 3I—for WT, FIG. 3J—for PPARα$^{-/-}$ and FIG. 3K—for PPAR/f-astrocytes). DAPI was used to stain nuclei. UN—No treatment. Scale bar=10 µM. (FIGS. 3L-3N) Mouse primary astrocytes isolated from PPARα$^{-/-}$ and PPARβ$^{-/-}$ and WT mice were treated with 25 µM gemfibrozil and 10 µM fenofibrate in serum free DMEM/F12 for 24 hrs. Whole cell extracts containing 5 µg total protein was incubated at 37° C. with 250 µM 7-amido-4-methylcoumarin in 96 well plates and readings were taken at an interval of 30, 45, 60, 90 and 120 mins. Mean values were taken and plotted in graphical format (FIG. 3L—for Wild type cells, FIG. 3M—for PPARα$^{-/-}$ cells and FIG. 3N—for PPARβ$^{-/-}$ cells). All results are mean±SEM of at least three independent experiments.

FIGS. 4A-4D show oral administration of gemfibrozil upregulates TPP1 in vivo in cortical and nigral astrocytes and neurons of WT and PPARβ$^{-/-}$, but not PPARα$^{-/-}$ mice. WT, PPARα$^{-/-}$ and PPARβ$^{-/-}$ mice (n=4 in each group) were treated with 7.5 mg/kg body wt/day of gemfibrozil (dissolved in 0.1% methylcellulose) or vehicle (0.1% methylcellulose) via gavage. After 21 d of treatment, mice were killed and cortical and nigral sections were double labeled for TPP1 (red) along with either GFAP (green) or NeuN (green) or TH (green). DAPI was used to visualize nucleus. (FIGS. 4A1-A3, 4B1-B3) TPP1 levels were compared between the astrocytes and neurons of the cortical sections of vehicle treated and gemfibrozil treated (FIG. 4A1, FIG. 4B1) WT, (FIGS. 4A2, 4B2) PPARα$^{-/-}$, & (A3, B3) PPARβ$^{-/-}$ mice. (FIGS. 4A1-4A3: GFAP and TPP1; FIGS. 4B1-4B3: NeuN and TPP1). Scale bar=20 µM. (FIGS. 4A4, 4B4) Higher magnification images showing co-localization of TPP1 and GFAP in the (FIG. 4A4) cortical astroglia and co-localization of NeuN and TPP1 in (FIG. 4B4) cortical neurons of gemfibrozil treated mice (WT and PPARβ$^{-/-}$). Scale bar=10 µM. (FIGS. 4C1-C3, 4D1-D3) TPP1 levels were compared between the astrocytes and neurons of the nigral sections of vehicle treated and gemfibrozil treated (FIGS. 4C1, 4D1) WT, (FIGS. 4C2, 4D2) PPARα$^{-/-}$ & (FIG. 4C3, FIG. 4D3) PPARβ$^{-/-}$ mice. Scale bar=20 µM. (C1-C3: GFAP and TPP1; FIGS. 4D1-D3: TH and TPP1). (FIG. 4C4, 4D4) Higher magnification images showing co-localization of TPP1 and GFAP in the (FIG. 4C4) nigral astroglia and co-localization of TH and TPP1 in (FIG. 4D4) nigral TH neurons of gemfibrozil treated mice (WT and PPARβ$^{-/-}$). Scale bar=10 µM. All results represent analysis of each of three cortical and nigral sections of each of four different mice per group.

FIGS. 5A-5H show oral administration of gemfibrozil upregulates TPP1 in vivo in the hippocampus of WT and PPARβ$^{-/-}$, but not PPARα$^{-/-}$ mice. WT, PPARα$^{-/-}$ and PPARβ$^{-/-}$ mice (n=4 in each group) were treated with 7.5 mg/kg body wt/day of gemfibrozil (dissolved in 0.1% methylcellulose) or vehicle (0.1% methylcellulose) via gavage. After 21 d of treatment, mice were killed and hippocampal (CA1 and dentate gyrus) sections were double labeled for TPP1 (red) and GFAP (green). DAPI was used to visualize nucleus. (FIGS. 5A-5C) TPP1 levels were compared between the dentate gyrus region of vehicle treated and gemfibrozil treated (FIG. 5A) WT, (FIG. 5B) PPARα$^{-/-}$, &

(FIG. 5C) PPARβ−/− mice. Scale bar=20 μM. (FIG. 5D) Higher magnification images showing co localization of TPP1 and GFAP in the dentate gyrus of gemfibrozil treated mice (WT, PPARα−/− and PPARβ−/−). Scale bar=10 μM. (FIGS. 5E-5G) TPP1 levels were compared between the CA1 region of vehicle treated and gemfibrozil treated (FIG. 5E) WT, (FIG. 5F) PPARα−/− & (FIG. 5G) PPARβ−/− mice. Scale bar=20 μM. (FIG. 5H) Higher magnification images showing co-localization of TPP1 and GFAP in the CA1 region of gemfibrozil treated mice (WT, PPARα−/− and PPARβ−/−). Scale bar=10 μM. All results represent analysis of each of three hippocampal sections of each of four different mice per group.

FIGS. 6A-6I show upregulation of TPP1 by fibrate drugs involves both PPARα and RXRα. (FIGS. 6A-6C) Mouse primary astrocytes were treated with different concentrations of all-trans retinoic acid (RA) and gemfibrozil and the combination of the two in serum-free DMEM/F12 medium for 24 hrs followed by monitoring of mRNA expression of Cln2 by quantitative RT-PCR (FIG. 6A) and protein expression of TPP1 by Western blot (FIG. 6B). (FIG. 6C) Denistometric analysis of TPP1 (relative to β-actin) with RA and gemfibrozil treatment. $p<0.05$ vs WT control; $p^b<0.05$ vs 0.5 μM RA only treatment; $p^c<0.05$ vs 10 μM gemfibrozil only treatment. (FIGS. 6D, 6E) Mouse primary astrocytes were untransfected, transfected with scrambled siRNA (1.0 μg) or RXRα siRNA (1.0 μg) for 36 hrs followed by treatment with RA (0.5 μM) and gemfibrozil (10 μM) alone and in combination for 24 hrs serum free DMEM/F12 medium followed by RT-PCR for Rxrα, Rxrβ, Rxrγ (FIG. 6D) and quantitative real time PCR for Cln2 (FIG. 6E). $p^*<0.05$ vs untransfected control; $p^{}<0.05$ vs scrambled siRNA transfected control; $p^d<0.05$ vs untransfected-gemfibrozil treated sample; $p^e<0.05$ vs untransfected-RA treated sample; $p^f<0.05$ vs scrambled siRNA transfected-gemfibrozil treated sample; $p8<0.05$ vs scrambled siRNA transfected-RA treated sample; ns—not significant w.r.t. RXR-α siRNA transfected control. (FIG. 6F) Mouse primary astrocytes were transfected with scrambled siRNA (1.0 μg) or RXRα siRNA (1.0 μg) and treated with gemfibrozil (10 μM) and RA (0.5 μM) alone and in combination under similar culture conditions and the protein expression of TPP1 were estimated by Western blot. (FIG. 6G) Denistometric analysis of TPP1 (relative to β-actin) with RA and gemfibrozil treatment. $p^{}<0.05$ vs scrambled siRNA transfected control; $p^h<0.05$ vs only gemfibrozil treatment; $p^i<0.05$ vs only RA treatment; ns—not significant w.r.t. RXR-α siRNA transfected control. (FIG. 6H) Mouse primary astrocytes isolated from wild type, PPARα−/− and PPARβ−/− mice were treated with RA (0.5 μM) alone and in combination with gemfibrozil (10 μM) under similar culture conditions and cells were subjected to Western blot for TPP1. (FIG. 6I) Densitometric analysis of TPP1 levels (relative to β-Actin) in PPARα−/− and PPARβ−/− and wild type astrocytes after RA and gemfibrozil+RA treatment. $p^†<0.05$ vs WT control; $p^{††}<0.05$ vs PPARβ−/− control; $p^j<0.05$ vs only RA treatment in WT cells; $p^k<0.05$ vs only RA treatment in PPARβ−/− cells; ns—not significant w.r.t. PPARα−/− control. All results are mean±SEM of at least three independent experiments.

(FIG. 7A) Mouse primary astrocytes were treated with gemfibrozil (10 μM) and RA (0.5 μM) alone and in combination in serum free DMEM/F12 for 6 hrs and the nuclear extract was subjected to (i) immunoprecipitation by PPARα Ab followed by immunoblot for both RXRα and PPARα, (ii) immunoprecipitation by RXRα Ab followed by immunoblot for both PPARα and RXRα, (iii) immunoprecipitation by control IgG followed by immunoblot for both PPARα and RXRα, (iv) nuclear extract was subjected to immunoblot for PPARα, RXRα and Histone3 (H3). (FIG. 7B) Schematic diagram for RXR binding site on the Cln2 promoter with the core sequence and amplicon length. (FIG. 7C) Mouse astrocytes were treated with the combination of gemfibrozil (10 μM) and RA (0.5 μM) for 6 hrs and recruitment of PPARα and RXRα on the RXR binding site of Cln2 promoter was monitored by ChIP analysis as described under "Materials and Methods". Normal IgG was used as control. All results are representative of at least there independent experiments.

FIGS. 13A-13C show the upregulation of lysosomal genes in brain cells by gemfibrozil and fenofibrate. (FIG. 13A) Quantitative real-time PCR for lysosomal genes in mouse astrocytes treated with 25 μM gemfibrozil for different time points under serum free conditions. Results are mean±SD of three different experiments. $^a p<0.001$ vs control. (FIG. 13B) RT-PCR for lysosomal genes in human astrocytes treated under same condition. (FIG. 13C) Human neurons were treated with different concentrations of fenofibrate for 24 hrs under serum free conditions and RT-PCR was done lysosomal genes. Results represent 3 independent experiments.

DETAILED DESCRIPTION

Figure 6F:
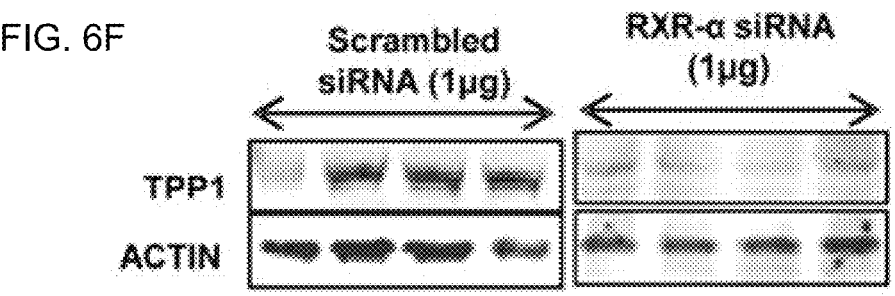

The present invention relates to methods of treatment of neuronal ceroid lipofuscinosis (NCL). Neuronal ceroid lipofuscinosis includes a group of diseases such as late infantile neuronal ceroid lipofuscinosis (LINCL) and Batten disease that are neurodegenerative lysosomal storage diseases. Many forms of NCL occur via mutations in the Cln genes. LINCL is associated with mutations in the Cln2 gene, which encodes tripeptidyl peptidase 1 (TPP1). The genes Cln1 and Cln3 are associated with infantile NCL (INCL) and juvenile NCL (JNCL), respectively.

The methods of the present invention include administering to a subject suffering from NCL an agent that upregulates or enhances expression from a gene such as Cln1, Cln2, Cln3, and/or any combination thereof. Upregulation may include increasing mRNA levels for Cln1, Cln2, Cln3, and/or any combination thereof.

The methods of the present invention also include administering to a subject suffering from NCL an agent that upregulates TPP1 or restores TPP1 activity. Upregulation may include increasing TPP1 mRNA levels, increasing TPP1 proteins levels, or increasing TPP1 enzymatic activity. The inventors have also discovered that activating a PPARα/RXRα heterodimer results in upregulation of TPP1. The inventors have also surprisingly shown that TPP1 is upregulated through the activity or involvement of PPARα, but not PPARβ or PPARγ.

The agent may be a lipid-lowering drug such as a fibrate. The fibrate may be gemfibrozil, fenofibrate, or clofibrate. Alternatively, the agent may be all-trans retinoic acid. Surprisingly and unexpectedly, administration of the fibrate in combination with all-trans retinoic acid to the subject upregulates TPP1 more than administration of the fibrate or all-trans retinoic acid alone. The fibrate and all-trans retinoic acid, when administered together to the subject, cooperatively enhance upregulation of TPP1. In other words, a lower dose of the fibrate is needed in the presence of all-trans retinoic acid to achieve the same degree of TPP1 upregulation as occurs when only a higher dose of the fibrate is administered to the subject.

Both gemfibrozil and fenofibrate are capable of enhancing TPP1 in cultured neurons and glial cells and in vivo in the brain. In addition, PPARα, but not PPARβ and PPARγ, is involved in gemfibrozil- and fenofibrate-mediated upregulation of TPP1. Furthermore, fibrate drugs upregulate TPP1 via activation of PPARα-RXRα heterodimer. Collectively, gemfibrozil and fenofibrate, FDA-approved drugs for hyperlipidemia, are of therapeutic value in the treatment of LINCL.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. METHODS OF TREATING A NEURODEGENERATIVE DISEASE

Provided herein is a method of treating a neurodegenerative disease. The neurodegenerative disease may be, for example, neuronal ceroid lipofuscinosis, Alzheimer's disease, Huntington's disease, Amyotrophic lateral sclerosis (ALS), Parkinson's disease, including Parkinson's plus diseases such as multiple system atrophy (MSA), progressive supranuclear palsy (PSP), corticobasal degeneration (CBD) or dementia with Lewy bodies (DLB). The neurodegenerative disorder may be characterized by defective autophage. Such disorders include Alzheimer's, Parkinson's disease, and Huntington's disease. The neurodegenerative disease may be a lysosomal storage disorder. The lysosomal storage disorder may be, for example, Tay-Sach's disease, Fabry disease, Niemann-Pick disease, Gaucher disease, Hunter Syndrome, Alpha-mannosidosis, Aspartylglucosaminuria, Cholesteryl ester storage disease, Chronic Hexosaminidase A Deficiency, Cystinosis, Danon disease, Farber disease, Fucosidosis, or Galactosialidosis.

The neuronal ceroid lipofuscinosis may be LINCL or Batten disease, for example. The method may include administering to a subject suffering from NCL an agent that upregulates TPP1 or restores TPP1 activity. The method may also include administering to a subject suffering from NCL an agent that upregulates or enhances expression from a gene such as Cln1, Cln2, Cln3, and/or any combination thereof.

NCL is a group of neurodegenerative diseases comprising typical autosomal recessive lysosomal storage disorders. NCLs may include clinical manifestations such as progressive mental deterioration, cognitive impairment, visual failure, seizures, and deteriorating motor function. NCLs may be associated with accumulation of autofluoroscent storage materials in neurons and/or other types of cells. NCLs may be divided into several types including Types 1 to 10, and the types may be based on the age of onset, ultra structural variations in accumulated storage materials, and genetic alterations. Presently, no established treatment and/or drugs are available for treatment of NCLs. Rather, present treatment is merely supportive of disease symptoms.

Many types of NCL may be associated with mutations in the Cln genes. These mutations may be associated with a deficiency or loss of function. For example, late infantile neuronal ceroid lipofuscinosis (LINCL) may be associated with mutations in the gene Cln2, while infantile NCL (INCL) and juvenile (JNCL) may be associated with mutations in the genes Cln1 and Cln3, respectively. The gene Cln2 encodes lysosomal tripeptidyl tripeptidase 1 (TPP1), which is a 46 kilodalton protein that functions in the acidic environment of the lysosomal compartment of a cell to remove tripeptides from the amino termini of proteins. Deficiency and/or loss of function of TPP1 may lead to intralysosomal accumulation of autofluorescent lipopigments known as ceroid-lipofuscins. Some subjects suffering from NCL may have residual activity of TPP1.

a. Agent

The agent may be a lipid-lowering drug, all-trans retinoic acid, or a combination of the lipid-lowering drug and all-trans retinoic acid. Administration of the agent to a subject suffering from NCL may upregulate or enhance expression from a gene such as Cln1, Cln2, Cln3, and/or any combination thereof. Upregulation may include increasing mRNA levels for Cln1, Cln2, Cln3, and/or any combination thereof.

Administration of the agent to a subject suffering from NCL may also upregulate TPP1 or restore TPP1 activity. Upregulation of TPP1 may include increasing the levels of TPP1 mRNA, increasing the levels of TPP1 protein, or increasing the enzymatic activity of TPP1. Additionally, upregulation of TPP1 may include activating the PPARα/RXRα heterodimer, which is recruited to the promoter of the Cln2 gene to affect TPP1 upregulation.

(1) Lipid-Lowering Drug

The agent mediating upregulation of TPP1 may be a lipid-lowering drug. Lipid-lowering drugs may be drugs that reduce the level of triglycerides circulating in the blood of the subject. Additionally, lipid-lowering drugs may be drugs that decrease the risk of hyperlipidemia. Such lipid-lowering drugs may include fibrates such as gemfibrozil, fenofibrate, and clofibrate.

The fibrate may mediate upregulation of TPP1 via PPARα, but not PPARβ and PPARγ. During upregulation of TPP1, PPARα forms a heterodimer with RXR-α and the RXR-α/PPAR-α heterodimer is recruited to the promoter of the Cln2 gene via a RXR binding site.

(2) All-Trans Retinoic Acid

The agent mediating upregulation of TPP1 may be all-trans retinoic acid. All-trans retinoic acid may also be known as ATRA, retinoic acid, tretinoin, and vitamin A acid. All-trans retinoic acid may mediate upregulation of TPP1 via the retinoid X receptor-α (RXR-α). During upregulation of TPP1, RXR-α forms a heterodimer with peroxisome proliferator-activated receptor-α (PPAR-α) and the RXR-α/PPAR-α heterodimer is recruited to the promoter of the Cln2 gene via a RXR binding site.

(3) Combination of Lipid-Lowering Drug and all-Trans Retinoic Acid

The agent mediating upregulation of TPP1 may comprise a combination of the lipid-lowering drug and all-trans retinoic acid. Such a combination may cooperatively mediate or enhance upregulation of TPP1 as compared to administration of the lipid-lowering drug or all-trans retinoic acid alone. The combination may cooperatively enhance upregulation of TPP1 about 2-fold, about 3-fold, about 4-fold, about 5-fold, or about 10-fold as compared to administration of the lipid-lowering drug or all-trans retinoic acid alone. Particularly, the combination may cooperatively enhance upregulation of TPP1 about 3-fold as compared to administration of the lipid-lowering drug or all-trans retinoic acid alone.

b. Pharmaceutical Compositions

The agent may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of the agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of gemfibrozil may be about 5 mg to about 2000 mg, about 10 mg to about 1900 mg, about 15 mg to about 1800 mg, about 20 mg to about 1700 mg, about 25 mg to about 1600 mg, about 30 mg to about 1500 mg, about 35 mg to about 1400 mg, about 40 mg to about 1300 mg, about 45 mg to about 1200 mg, about 50 mg to about 1100 mg, about 55 mg to about 1000 mg, about 60 mg to about 900 mg, about 65 mg to about 800 mg, about 70 mg to about 700 mg, about 75 mg to about 600 mg, about 80 mg to about 500 mg, about 85 mg to about 400 mg, about 90 mg to about 300 mg, about 95 mg to about 200 mg, or about 100 mg to about 175 mg. In another example, the therapeutically effective amount of gemfibrozil may be about 600 mg or about 1200 mg.

For example, a therapeutically effective amount of fenofibrate may be about 5 mg to about 2000 mg, about 10 mg to about 1900 mg, about 15 mg to about 1800 mg, about 20 mg to about 1700 mg, about 25 mg to about 1600 mg, about 30 mg to about 1500 mg, about 35 mg to about 1400 mg, about 40 mg to about 1300 mg, about 45 mg to about 1200 mg, about 50 mg to about 1100 mg, about 55 mg to about 1000 mg, about 60 mg to about 900 mg, about 65 mg to about 800 mg, about 70 mg to about 700 mg, about 75 mg to about 600 mg, about 80 mg to about 500 mg, about 85 mg to about 400 mg, about 90 mg to about 300 mg, about 95 mg to about 200 mg, or about 100 mg to about 175 mg. In another example, the therapeutically effective amount of fenofibrate may be about 40 mg, about 48 mg, about 54 mg, about 67 mg, about 100 mg, about 120 mg, about 134 mg, about 145 mg, about 160 mg, or about 200 mg.

For example, a therapeutically effective amount of clofibrate may be about 5 mg to about 2000 mg, about 10 mg to about 1900 mg, about 15 mg to about 1800 mg, about 20 mg to about 1700 mg, about 25 mg to about 1600 mg, about 30 mg to about 1500 mg, about 35 mg to about 1400 mg, about 40 mg to about 1300 mg, about 45 mg to about 1200 mg, about 50 mg to about 1100 mg, about 55 mg to about 1000 mg, about 60 mg to about 900 mg, about 65 mg to about 800 mg, about 70 mg to about 700 mg, about 75 mg to about 600 mg, about 80 mg to about 500 mg, about 85 mg to about 400 mg, about 90 mg to about 300 mg, about 95 mg to about 200 mg, or about 100 mg to about 175 mg. In another example, the therapeutically effective amount of clofibrate may be about 500 mg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

c. Modes of Administration

Methods of treating neuronal ceroid lipofuscinosis may include any number of modes of administering the agent or pharmaceutical compositions of the agent. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixiers, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate, composition.

For parenteral administration, the agent or pharmaceutical compositions of the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration the agent or pharmaceutical compositions of the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

The present invention has multiple aspects, illustrated by the following non-limiting examples.

3. EXAMPLES

Example 1

Materials and Methods for Examples 2-9

Reagents:

DMEM/F-12 50/50 1×, Hank's balanced salt solution (HBSS) and 0.05% trypsin were purchased from Mediatech (Washington, D.C.). Fetal bovine serum (FBS) was obtained from Atlas Biologicals (Fort Collins, Colo.). Antibiotic-antimycotic, gemfibrozil and Akt-inhibitor (Akt-i) were obtained from Sigma-Aldrich (St. Louis, Mo.). Wortmannin and LY294002 were purchased from Calbiochem (Darmstadt, Germany).

Isolation of Mouse Primary Astroglia:

Astroglia were isolated from mixed glial cultures as described (17,18) according to the procedure of Giulian and Baker (19). Briefly, on day 9, the mixed glial cultures were washed three times with Dulbecco's modified Eagle's medium/F-12 and subjected to shaking at 240 rpm for 2 h at 37° C. on a rotary shaker to remove microglia. After 2 days, the shaking was repeated for 24 h for the removal of oligodendroglia and to ensure the complete removal of all nonastroglial cells. The attached cells were seeded onto new plates for further studies.

Isolation of Primary Human Astroglia:

Primary human astroglia were prepared as described (20,21). All experimental protocols were reviewed and approved by the Institutional Review Board of the Rush University Medical Center. Briefly, 11- to 17-week-old fetal brains obtained from the Human Embryology Laboratory (University of Washington, Seattle, Wash., USA) were dissociated by trituration and trypsinization. On 9th day, these mixed glial cultures were placed on a rotary shaker at 240 rpm at 37° C. for 2 h to remove loosely attached microglia. On $11^{th}$ day, the flasks were shaken again at 190 rpm at 37° C. for 18 h to remove oligodendroglia. The attached cells remaining were primarily astrocytes. These cells were trypsinized and subcultured in complete media at 37° C. with 5% $CO_2$ in air to yield more viable and healthy cells. By immunofluorescence assay, these cultures homogeneously expressed GFAP, a marker for astrocytes (22).

Isolation of Neurons from Different Brain Regions:

Fetal (E18-E16) mouse neurons were prepared as previously described (23) with modifications. Whole brains were removed and cortical, hippocampal, striatal and cerebellar fractions were dissected in serum free Neurobasal media. The cells were washed by centrifugation three times at 1200 rpm for 10 min, the pellet dissociated and the cells plated at 10% confluence in 8-well chamber slides pre-treated for >2 hr with Poly-D-Lysine (Sigma, St. Louis, Mo.). After 4 min, the non-adherent cell suspension was aspirated and 500 ml complete Neurobasal media (Invitrogen) supplemented with 2% B27 was added to each well. The cells were incubated for 4 days prior to experimentation. Double-label immunofluorescence with β-tubulin and either GFAP or CD11b revealed that neurons were more than 98% pure (data not shown). The cells were stimulated with gemfibrozil in Neurobasal media supplemented with 2% B27 minus antioxidants (Invitrogen) for 24 hr prior to methanol fixation and immunostaining.

Semi-Quantitative Reverse Transcriptase-Coupled Polymerase Chain Reaction (RT-PCR):

Total RNA was isolated from mouse primary astrocytes and human primary astrocytes using RNA-Easy Qiagen (Valencia, Calif.) kit following manufactures protocol. Semi-quantitative RT-PCR was carried out as described earlier (24) using oligo (dT) 12-18 as primer and moloney murine leukemia virus reverse transcriptase (MMLV-RT, Invitrogen) in a 20 µl reaction mixture. The resulting cDNA was appropriately amplified using Promega Master Mix (Madison, Wis.) and the following primers (Invitrogen) for murine genes:

```
Mouse Cln1:
Sense,
                               (SEQ ID NO: 1)
5'-ACACAGAGGACCGCCTGGGG-3'

Antisense,
                               (SEQ ID NO: 2)
5'-TCATGCACGGCCCACACAGC-3'

Mouse Cln2:
Sense,
                               (SEQ ID NO: 3)
5'-CACCATCCAGTTACTTCAATGC-3'

Antisense,
                               (SEQ ID NO: 4)
5'-CTGACCCTCCACTTCTTCATTC-3'

Mouse Cln3:
Sense,
                               (SEQ ID NO: 5)
5'-TGCTGCCCTGCCATCGAGTG-3'

Antisense,
                               (SEQ ID NO: 6)
5'-GGCAGCGCTCAGCATCACCA-3'

Mouse Gapdh:
Sense,
                               (SEQ ID NO: 7)
5'-GCACAGTCAAGGCCGAGAAT-3'

Antisense,
                               (SEQ ID NO: 8)
5'-GCCTTCTCCATGGTGGTGAA-3'
```

Amplified products were electrophoresed on 2% agarose (Invitrogen) gels and visualized by ethidium bromide (Invitrogen) staining. Glyceraldehyde-3-phosphate dehydrogenase (Gapdh) mRNA was used as a loading control to ascertain that an equivalent amount of cDNA was synthesized from each sample.

Quantitative Real-Time PCR:

The mRNA quantification was performed using the ABI-Prism7700 sequence detection system (Applied Biosystems, Foster City, Calif.) using iTaq™ Fast Supermix With ROX (Bio-Rad, Hercules, Calif.) and the following 6-FAM/ZEN/IBFQ-labeled primers for murine genes: Cln2 and Gapdh (Integrated DNA Technologies Coralville, Iowa). The mRNA expression of the targeted genes was normalized to the level of Gapdh mRNA and data was processed by the ABI Sequence Detection System 1.6 software.

Immunostaining of Cells:

Immunocytochemistry was performed as described earlier (25). Briefly, 8 well chamber slides containing mouse primary astrocytes, mouse neurons, human primary astrocytes or SH-SY5Y cells were cultured to 70-80% confluence were fixed with chilled Methanol (Fisher Scientific, Waltham, Mass.) overnight, followed by two brief rinses with filtered PBS. Samples were blocked with 2% BSA (Fisher Scientific) in PBS containing Tween 20 (Sigma) and Triton X-100 (Sigma) for 30 min and incubated at room temperature under shaking conditions for 2 hr in PBS containing the following anti-mouse primary antibodies: TPP1 (1:200; Santa Cruz Biotech, Santa Cruz, Calif.), GFAP, (1:100; Santa Cruz), and 3-tubulin (1:5000; Millipore). After four 15 min washes in filtered PBS, the slides were further incubated with Cy2 or Cy5-labeled secondary antibodies (all 1:200; Jackson ImmunoResearch, West Grove, Pa.) for 1 hr under similar shaking conditions. Following four 15 minute washes with filtered PBS, cells were incubated for 4-5 min with 4', 6-diamidino-2-phenylindole (DAPI, 1:10,000; Sigma). The samples were run in an EtOH and Xylene (Fisher) gradient, mounted and observed under Olympus BX41 fluorescence microscope.

Immunostaining of Tissue Sections:

After 21 days of treatment, mice were sacrificed and their brains fixed, embedded, and processed. Sections were made from different brain regions and for immunofluorescence staining on fresh frozen sections, anti-mouse TPP1 (1:200), goat anti mouse GFAP (1:100) were used. The samples were mounted and observed under Olympus BX41 fluorescence microscope (26).

Immunoblotting:

Western blotting was conducted as described earlier (27, 28) with modifications. Briefly, cells were scraped in double-distilled $H_2O$ and sodium dodecyl sulfate (SDS), electrophoresed on NuPAGE® Novex® 4-12% Bis-Tris gels (Invitrogen) and proteins transferred onto a nitrocellulose membrane (Bio-Rad) using the Thermo-Pierce Fast Semi-Dry Blotter. The membrane was then washed for 15 min in TBS plus Tween 20 (TBST) and blocked for 1 hr in TBST containing BSA. Next, membranes were incubated overnight at 4° C. under shaking conditions with the following 1° antibodies; TPP1 (1:250, Santa Cruz), β-actin (1:800; Abcam, Cambridge, Mass. The next day, membranes were washed in TBST for 1 hr, incubated in 2° antibodies against 1° antibody hosts (all 1:10,000; Jackson ImmunoResearch) for 1 hr at room temperature, washed for one more hour and visualized under the Odyssey® Infrared Imaging System (Li-COR, Lincoln, Nebr.).

TPP1 Activity Assay:

TPP-I activity was assayed in 96-well format plates using the following modification of the method described by Vines and Warburton (6). Briefly, samples and substrate (40 µL) were mixed in individual wells of polystyrene 96-well plate (Nalge Nunc International). The substrate solution consisted of 250 µmol/L Ala-Ala-Phe 7-amido-4-methylcoumarin (cat. no. A3401; Sigma; diluted freshly from a 25 mmol/L stock solution in dimethyl sulfoxide stored at −20° C.) in 0.15 mol/L NaCl-1 g/L Triton X-100-0.1 mol/L sodium acetate, adjusted to pH 4.0 at 20° C. Plates were centrifuged briefly to dispel bubbles and placed in a 37° C. Plates were mixed for 10 s before each reading. The plates were read from the bottom using 360/20 nm excitation and 460/25 nm emission filters. Prior to the assay, the optimum substrate concentration and total protein in cell extract that can used to get best results were determined in the same manner described above, using different substrate concentrations and protein concentrations in the cell extract.

Immunoprecipitation from Nuclear Extract:

After treatment, cells were washed with PBS, scraped into 1.5 mL tubes and centrifuged in 4° C. for 5 min at 500 rpm. The supernatant was aspirated and the pellet was resuspended in a membrane lysis buffer comprised of (4-(2-hydroxyethyl)-1-piperazineethanesulfonic acid) (HEPES, pH 8.0), $MgCl_2$, KCl, dithiothreitol (DTT) and protease/phosphatase inhibitors, vortexed and centrifuged in 4° C. at 15,000 rpm for 3 minutes. Again, the supernatant was aspirated and the pellet was resuspended in a high salt, nuclear envelope lysis buffer comprised of HEPES (pH 8.0), $MgCl_2$, glycerol, NaCl, ethylenediaminetetraacetic acid (EDTA), DTT and protease/phosphatase inhibitors, rotated vigorously in 4° C. for 30 min and centrifuged in 4° C. at 15,000 rpm for 15 minutes. The resultant nuclear pellet was resuspended in IP buffer and a fraction was kept separately as lysate. The remaining nuclear extract was then precleared with 25 ul of protein A-agarose (50%, v/v). The supernatants were immunoprecipitated with 5 ug of anti-RXRα or anti-PPARα or normal IgG (Santa Cruz Biotechnology, Inc.) overnight at 4 C, followed by incubation with protein A-agarose for 4 hrs at 4° C. Protein A-agarose-antigen-antibody complexes were collected by centrifugation at 12,000 rpm for 60 s at 4° C. The pellets were washed five times with 1 ml of IP buffer (20 Mm Tris-HCl, pH 8.0, 137 mM NaCl, 2 mM EDTA, 1% Nonidet P-40, 10% glycerol, 0.1 mM phenylmethylsulfonyl fluoride) for 20 min each time at 4° C. Bound proteins were resolved by SDS-PAGE, followed by Western blotting with the anti-RXRα (1:2000, Santa Cruz) and/or anti-PPARα (1:250, Santa Cruz). The lysate was resolved by SDS-PAGE followed by immunoblot for PPARα, RXRα and H3.

Chromatin Immunoprecipitation Assay:

ChIP assays were performed using method described by Nelson et al (29), with certain modifications. Briefly, mouse primary astrocytes were stimulated by 10 uM gemfibrozil and 0.5 μM RA together for 6 hrs followed by fixing with formaldehyde (1.42% final volume) and quenching with 125 mM Glycine. The cells were pelleted and lysed in IP buffer containing 150 mM NaCl, 50 mM Tris-HCl (pH 7.5), 5 mM EDTA, NP-40 (0.5% vol/vol), Triton X-100 (1.0% vol/vol). For 500 ml, add 4.383 g NaCl, 25 ml of 100 mM EDTA (pH 8.0), 25 ml of 1 M Tris-HCl (pH 7.5), 25 ml of 10% (vol/vol) NP-40 and 50 ml of 10% (vol/vol) Triton X-100 containing the following inhibitors; 10 μg/ml leupeptin, 0.5 mM phenylmethylsulfonyl fluoride (PMSF), 30 mM p-nitrophenyl phosphate, 10 mM NaF, 0.1 mM $Na_3VO_4$, 0.1 mM $Na_2MoO_4$ and 10 mM β-glycerophosphate. After one wash with 1.0 ml IP buffer the pellet was resuspended in 1 ml IP buffer (containing all inhibitors) and sonicated and sheared chromatin was split into two fractions (one to be used as Input). The remaining fraction was incubated overnight under rotation at 4° C. with 5-7 μg of anti-PPARα or anti-RXRα Abs or normal IgG (Santa Cruz) followed by incubation with Protein G-Agarose (Santa Cruz) for 2 hrs at 4° C. under rotation. Beads were then washed five times with cold IP buffer and a total of 100 μl of 10% Chelex (10 g/100 ml H2O) is added directly to the washed protein G beads and vortexed. After 10 min boiling, the Chelex/protein G bead suspension is allowed to cool to room temperature. Proteinase K (100 μg/ml) is then added and beads are incubated for 30 min at 55° C. while shaking, followed by another round of boiling for 10 min. Suspension is centrifuged and supernatant is collected. The Chelex/protein G beads fraction is vortexed with another 100 μl water, centrifuged again, and the first and the second supernatants are combined. Eluate is used directly as a template in PCR. The following primers were used to amplify fragments flanking RXR binding element in the mouse Cln2 promoter: Set1: sense: 5'-CAG CTG CCA TGT CCC CCA GC-3', (SEQ ID NO: 9) antisense: 5'-TGC GCA GCT CTG TGT CAT CCG-3' (SEQ ID NO: 10); Set2: sense: 5'-GCT CCC TCT CCT CAG CTG CCA-3' (SEQ ID NO: 11), antisense: 5'-CAT CCG GAG GCT CCA GGC CA-3' (SEQ ID NO: 12). The PCRs were repeated by using varying cycle numbers and different amounts of templates to ensure that results were in the linear range of PCR.

Densitometric Analysis:

Protein blots were analyzed using ImageJ (NIH, Bethesda, Md.) and bands were normalized to their respective β-actin loading controls. Data are representative of the average fold change with respect to control for three independent experiments.

Statistics:

Values are expressed as means±SEM of at least three independent experiments. Statistical analyses for differences were performed via Student's T-test. This criterion for statistical significance was $p<0.05$.

Example 2

Fibrate Drugs Upregulate TPP1 mRNA and Protein in Mouse Primary Astrocytes

There have been reports that residual TPP-I activity can be found in patients indicating that a few copies of normal Cln2 gene are left in patients affected with LINCL (8,9,30, 31). We examined if FDA-approved lipid-lowering drugs like gemfibrozil and fenofibrate were capable of upregulating the expression of TPP1 in brain cells. Mouse primary astrocytes were treated in serum free media with gemfibrozil with different doses and for different time points. Both RT-PCR and real-time quantitative PCR (qPCR) analyses clearly indicated that gemfibrozil upregulated Cln2 mRNA levels in mouse primary astrocytes in a time and dose dependant manner with maximum increase at 24 hrs of 25 μM gemfibrozil treatment (FIGS. 1A, 1B, 1C & 1D). Other lysosomal genes like Cln1 and Cln3 which are responsible for Infantile NCL (INCL) and Juvenile NCL (JNCL) respectively were also found to increase within 12 to 24 h (FIG. 1A). The mRNA data was validated by Western blot where 3-4 fold increase in TPP1 protein level was found with 25 μM gemfibrozil and 10 μM fenofibrate treatment for 24 hrs. (FIGS. 1E and 1F) Immunofluorescence of primary mouse astrocytes stimulated with gemfibrozil and fenofibrate also revealed a dose dependant increase in TPP1 protein (FIG. 1G).

Example 3

Gemfibrozil and Fenofibrate Upregulate TPP1 in Neurons from Different Parts of the Mouse Brain Lack of TPP 1 enzyme causes accumulation of lipofuscines in neurons leading to loss of neurons in brain causing the disease to progress (5). Hence we examined the effect of the fibrate drugs in neurons and determined whether the induction of TPP1 occurs throughout the brain. Mouse primary neurons were isolated from different brain regions viz. cortex, hippocampus, and striatum and cultured and treated with gemfibrozil and fenofibrate. The immunofluorescence showed a significant increase in the mouse neurons from all three brain regions (FIGS. 1H, 1J & 1L). Further, the neurons from those three brain regions were treated with gemfibrozil for 24 hrs followed by Western blotting for TPP1 which showed about 2-3 fold increase in TPP1 protein, as determined by densitometric quantification (FIGS. 1I, 1K & 1M).

Example 4

TPP1 Proteins Upregulated by the Fibrate Drugs are Functionally Active

Since the functional activity of the TPP1 protein is of critical importance in the clinical setting for LINCL (6), activity of the enzyme was measured. The cells were homogenized and the cell extracts were subjected to TPP1 activity assay. Prior to that, the optimal substrate concentration and optimal amount of extract for the assay was determined by using different concentrations of substrate and sample respectively (Supplementary FIGS. 1A & 1B). TPP1 activity was measured (as described in the methods section) in mouse primary neurons and mouse primary astrocytes. The product formation increased with increasing doses of treatment indicating an increase in activity of the protein in the cell extracts (FIGS. 1N & 1O). This can be attributed to the increase in the levels of proteins in the cells observed in the earlier experiments. Collectively, these data strongly suggest that fibrate drugs can enhance both the mRNA and protein levels resulting in an increased activity of the protein in the cell.

Example 5

Fibrate Drugs Upregulate TPP1 mRNA and Protein in Human Brain Cells

We further examined whether a similar increase in Cln2 mRNA and protein was obtained upon treatment of human cells with gemfibrozil and fenofibrate. Human astrocytes were treated in the same way as the mouse cells and the mRNA levels were quantified. Again, both RT and qPCR data indicated an increase in Cln2 mRNA levels in human astrocytes in a dose and time dependant manner with maximum at a dose of 25 uM gemfibrozil (~15 fold) and at 12 hrs (~10 fold) (FIGS. 2A, 2B, 2C & 2D). However, fenofibrate was seen to increase the mRNA levels at a relatively lower dose (10 uM) but at same time point (12 hrs) as that of gemfibrozil (FIGS. 2E & 2F). Once again, the protein levels were assessed in human astrocytes and SH-SY5Y cell lines by immunofluorescence and in both the cell types a considerable increase in the level of TPP1 protein was observed. (FIGS. 2G & 2H).

Example 6

PPARα is Involved in Fibrate Drug Mediated Upregulation of TPP1

Since it is known that PPARs are activated by fibrate drugs, the role of these receptors in mediating upregulation of TPP1 protein was examined (15). Astrocytes isolated from PPARα$^{-/-}$ and PPARβ$^{-/-}$ and wild-type (WT) mice were treated with gemfibrozil and fenofibrate and Cln2 mRNA levels measured. The data from semi-quantitative RT-PCR and qRT-PCR showed that WT and PPARβ$^{-/-}$ cells showed similar patterns of upregulation, whereas PPARα$^{-/-}$ cells showed little or no effect on the upregulation of Cln2 mRNA expression upon gemfibrozil treatment (FIGS. 3A and 3B) and fenofibrate treatment (FIGS. 3C and 3D). When mouse primary astrocytes were treated with GW9662, a PPARγ antagonist, followed by gemfibrozil or fenofibrate treatment, there was increased expression of Cln2 mRNA, even in presence of the antagonist (FIGS. 3G and 3H).

To confirm the mRNA measurements the WT and PPARα$^{-/-}$ and PPARβ$^{-/-}$ astrocytes were processed for protein analysis. The cells were treated similarly with gemfibrozil and fenofibrate and immunofluorescence and Western blotting were performed. The immunoblot and densitometric analysis of the blots showed no significant increase in TPP1 levels in PPARα$^{-/-}$ cells, but about 4-5 fold increase in WT and PPARβ$^{-/-}$ cells (FIGS. 3E and 3F). The data from the Western blot was confirmed by immunofluorescence where a similar effect of the drugs on WT and KO astrocytes was observed, i.e. little or no increase in TPP1 in PPARα$^{-/-}$ cells, compared to WT and PPARβ$^{-/-}$ cells (FIGS. 3I, 3J & 3K).

Furthermore, the presence of active TPP1 enzyme was also confirmed by measurement of TPP1 activity in WT and KO cell types. The enzymatic activity was drastically increased in WT and PPARβ$^{-/-}$ cells upon treatment with gemfibrozil or fenofibrate (FIGS. 3L and 3N), while PPARα$^{-/-}$ cell extracts showed no significant increase in TPP1 enzymatic activity (FIG. 3M). Collectively, these data indicate that PPARα, but neither PPARβ nor PPARγ, is involved in the gemfibrozil- and fenofibrate-mediated upregulation of TPP 1.

Example 7

TPP1 is Upregulated by Fibrate Drugs In Vivo in the CNS of WT and PPARβ$^{-/-}$, but not in PPARα$^{-/-}$, Mice Once we confirmed the involvement of PPARα in the fibrate mediated upregulation of TPP1 protein, we further checked whether the same results could be replicated in in vivo settings. WT, PPARα$^{-/-}$ and PPARβ$^{-/-}$ mice from same background were treated orally for 21 days with 7.5 mg/kg body wt/day gemfibrozil dissolved in 0.1% methylcellulose, which was also used as vehicle. At the end of the treatment, the mice were killed and different regions of their brain, viz. Substantia nigra pars compacta, cortex, hippocampus, and dentate gyrus were sectioned, and immunofluorescence was performed for the presence of TPP1. Gemfibrozil treatment markedly increased the level of TPP1 both in GFAP-positive cortical astrocytes (FIGS. 4 A1, A2, A3 & A4) and NeuN-positive cortical neurons (FIGS. 4 B1, B2, B3 & B4) in WT and PPARβ$^{-/-}$, but not PPARα$^{-/-}$, mice. Similarly, gemfibrozil treatment also increased the level of TPP1 in GFAP-positive astrocytes (FIGS. 4 C1, C2, C3 & C4) and tyrosine hydroxylase-positive neurons (FIGS. 4 D1, D2, D3 & D4) in the substantia nigra of WT and PPARβ$^{-/-}$, but not PPARα$^{-/-}$, mice. Gemfibrozil also increased TPP1 mostly in the non-neuronal cells in the dentate gyrus (FIGS. 5A, 5B, 5C & 5D) and CA1 region of the hippocampus (FIGS. 5E, 5F, 5G & 5H) of WT and PPARβ$^{-/-}$, but not PPARα$^{-/-}$, mice. These data clearly indicate that gemfibrozil increases TPP1 in vivo in the CNS via PPARα.

Example 8

Upregulation of TPP1 by Fibrate Drugs Involve Both PPARα and RXRα

Figure 6G:
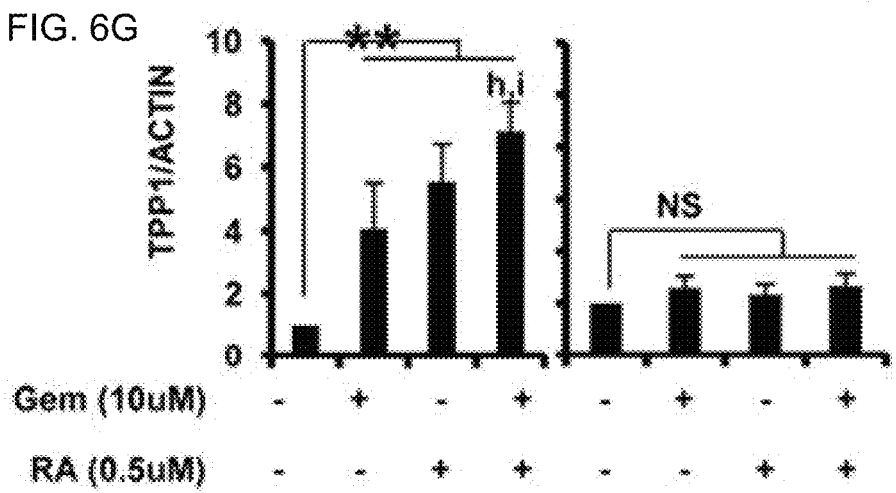
Figure 6H:
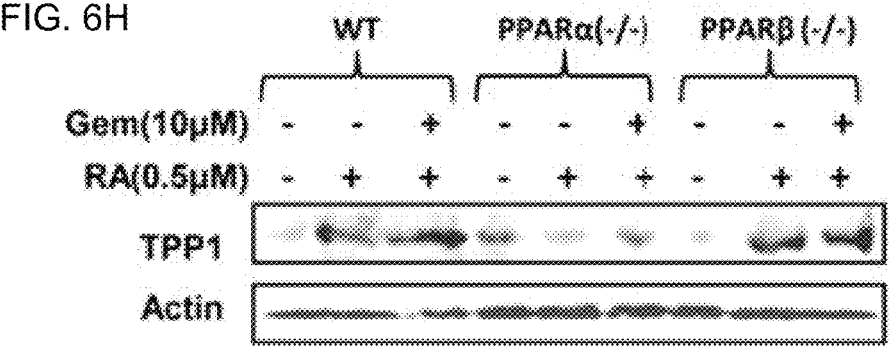
Figure 6I:
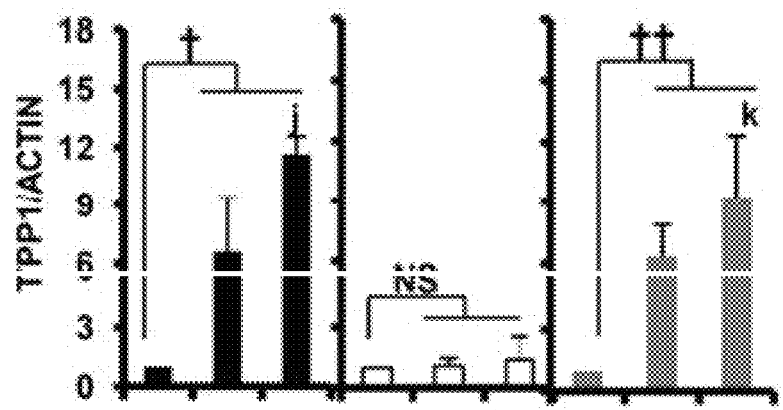

Next we investigated the mechanism of this upregulation. We observed that Cln2 gene promoter lacked PPAR binding site but contained a RXR binding site, instead. Due to the facts that RXRα is abundant in the brain and astrocytes (32,33) and that PPARα and RXRα form heterodimer, we thought the mechanism of upregulation of TPP1 may involve co-operative action of both PPARα and RXRα and not PPARα alone. To verify our hypothesis, we performed an array of experiments. First, we checked whether activating RXR by all-trans retinoic acid (RA), a known activator of RXRs, caused any change in the mRNA or protein levels of TPP1. Interestingly, quantitative real time PCR data showed that even RA alone enhanced the mRNA levels of Cln2 (FIG. 6A). RA at a concentration of 0.5 µM caused about 3.5 fold increase in Cln2 mRNA levels which is comparable to the effect of 10 µM gemfibrozil treatment (~4 fold) (FIG. 6A). Moreover, when cells were treated with low dose of gemfibrozil (10 µM) together with RA (at different concentrations), there was a profound increase in the Cln2 levels with optimum concentration of the combination being at 10 µM gemfibrozil and 0.5 µM RA (about 12 fold increase) (FIG. 6A). These mRNA data was validated by Western blot performed in mouse astrocytes using the similar treatments (FIG. 6B). The densitometry analysis showed similar pattern of increase in the protein levels of TPP1 as observed from the mRNA data (FIG. 6C). In both real-time PCR and immunoblot experiments the increase of TPP 1 expression with the combinatorial treatment (10 µM gemfibrozil and 0.5 µM RA) was found to be statistically significant when compared to either gemfibrozil (10 µM) or RA (0.5 µM) treatment alone. This finding clearly indicates the possible involvement of RXR in the upregulation of the Cln2 gene. Secondly, to confirm the involvement of RXRα, we knocked down RXRα in astrocytes by RXRα siRNA followed by treatment with gemfibrozil and RA. The siRNA was found to specifically knockdown RXRα, but neither RXRβ nor RXRγ (FIG. 6D). The effect of gemfibrozil and RA was found to be abrogated in the absence of RXRα, as observed from the quantitative real time PCR data (FIG. 6E). There was almost 8-10 fold increase in the Cln2 level in both untransfected cells as well as cells transfected with scrambled siRNA, whereas cells with RXRα knockdown were almost unresponsive to the treatment of gemfibrozil or RA alone as well as the combination (FIG. 6E). Similar results were obtained with the protein analysis. The denistometric analysis for the TPP1 Western blot showed almost no enhancement of TPP1 levels in RXRα siRNA transfected cells (FIGS. 6F & 6G). Finally, to validate our hypothesis that both PPARα and RXRα are involved in the upregulation process, we checked whether activation of RXRα alone (in the absence of PPARα) can induce the expression of Cln2. Mouse astrocytes from wild type (WT), PPARα$^{-/-}$ and PPARβ$^{-/-}$ mice were treated with RA (0.5 µM) and the combination of gemfibrozil (10 µM) and RA (0.5 µM) followed by immunoblot analysis for TPP 1. It was observed that neither RA alone nor the combination could induce TPP1 in PPARα$^{-/-}$ cells, whereas WT and PPARβ$^{-/-}$ cells were responsive to the treatment (about 5-6 fold induction of TPP1) (FIGS. 6H & 6I). These data suggest that either PPARα or RXRα alone is not sufficient for the upregulation of TPP1.

Example 9

Fibrate Drugs Upregulate TPP1 Via Activation of PPARα/RXRα Heterodimer

Figures 7A, 7B, 7C:
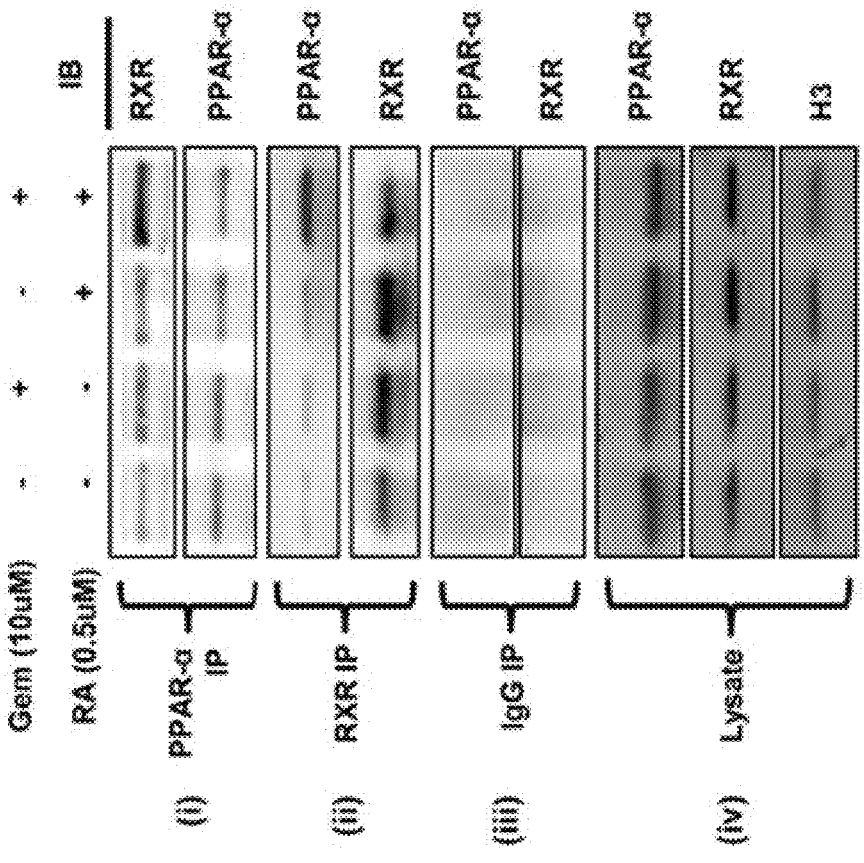
FIGS. 7A-7C show fibrate drugs upregulating TPP1 via activation of PPARα/RXRα heterodimer.
Figure 8:
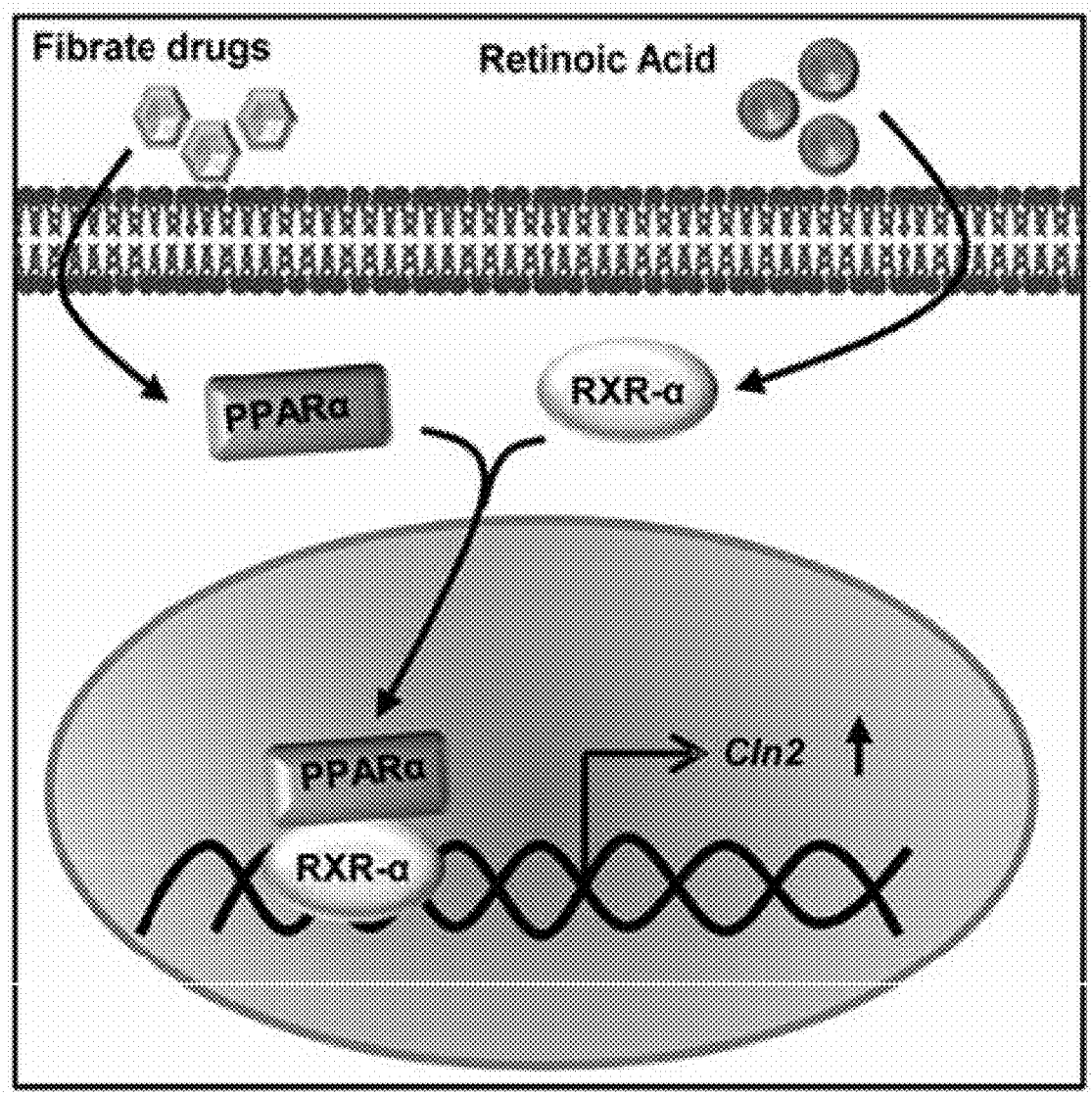
FIG. 8 is a schematic representation of the mechanism of upregulation of TPP1 by fibrate drugs via PPARα/RXRα pathway.
Figure 9:
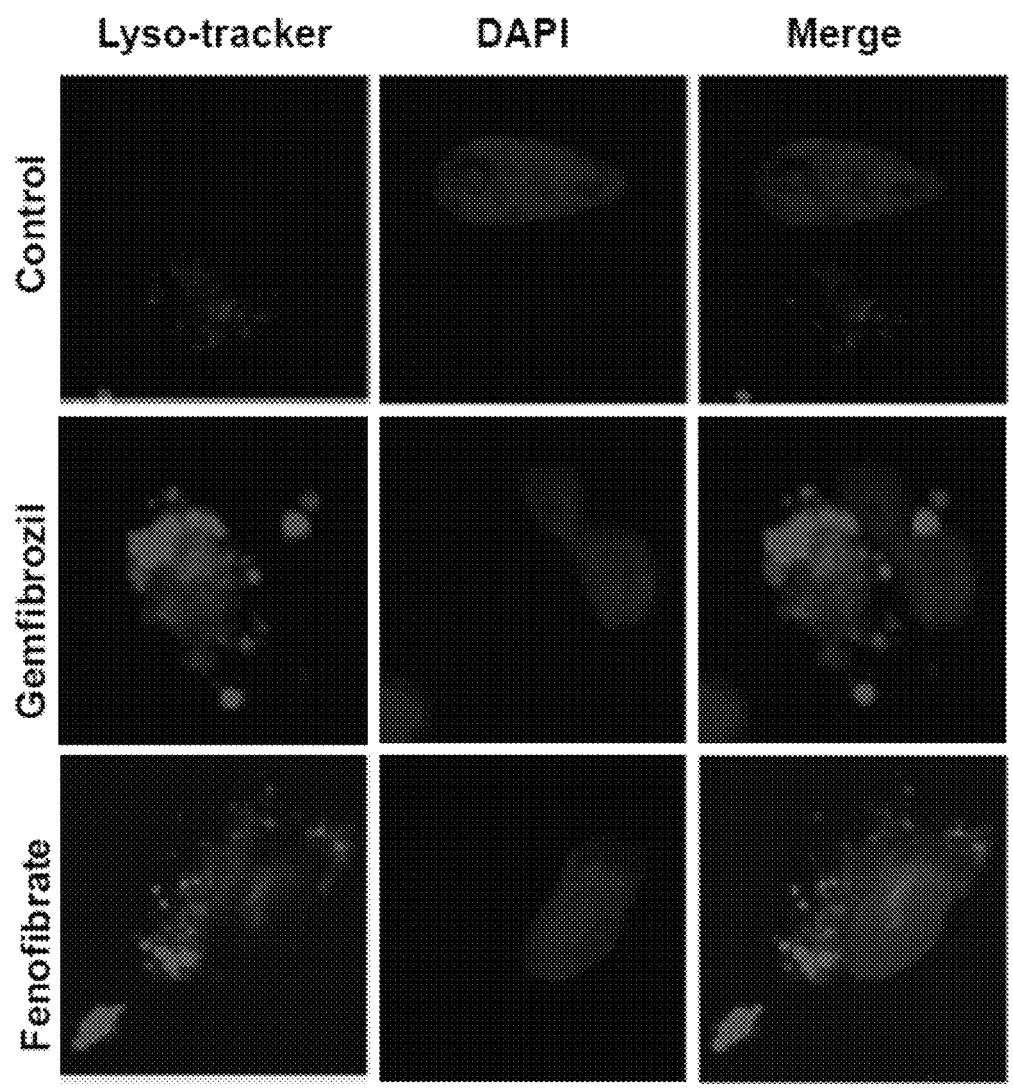
FIG. 9 shows the upregulation of lysosomal proliferation in primary human astrocytes by gemfibrozil and fenofibrate. Cells were treated with 25 μM gembibrozil and 10 μM fenofibrate for 24 hrs followed by labeling lysosomes with LysoTracker. DAPI was used to visualize nuclei. Results represent 3 independent experiments.
Figure 10:
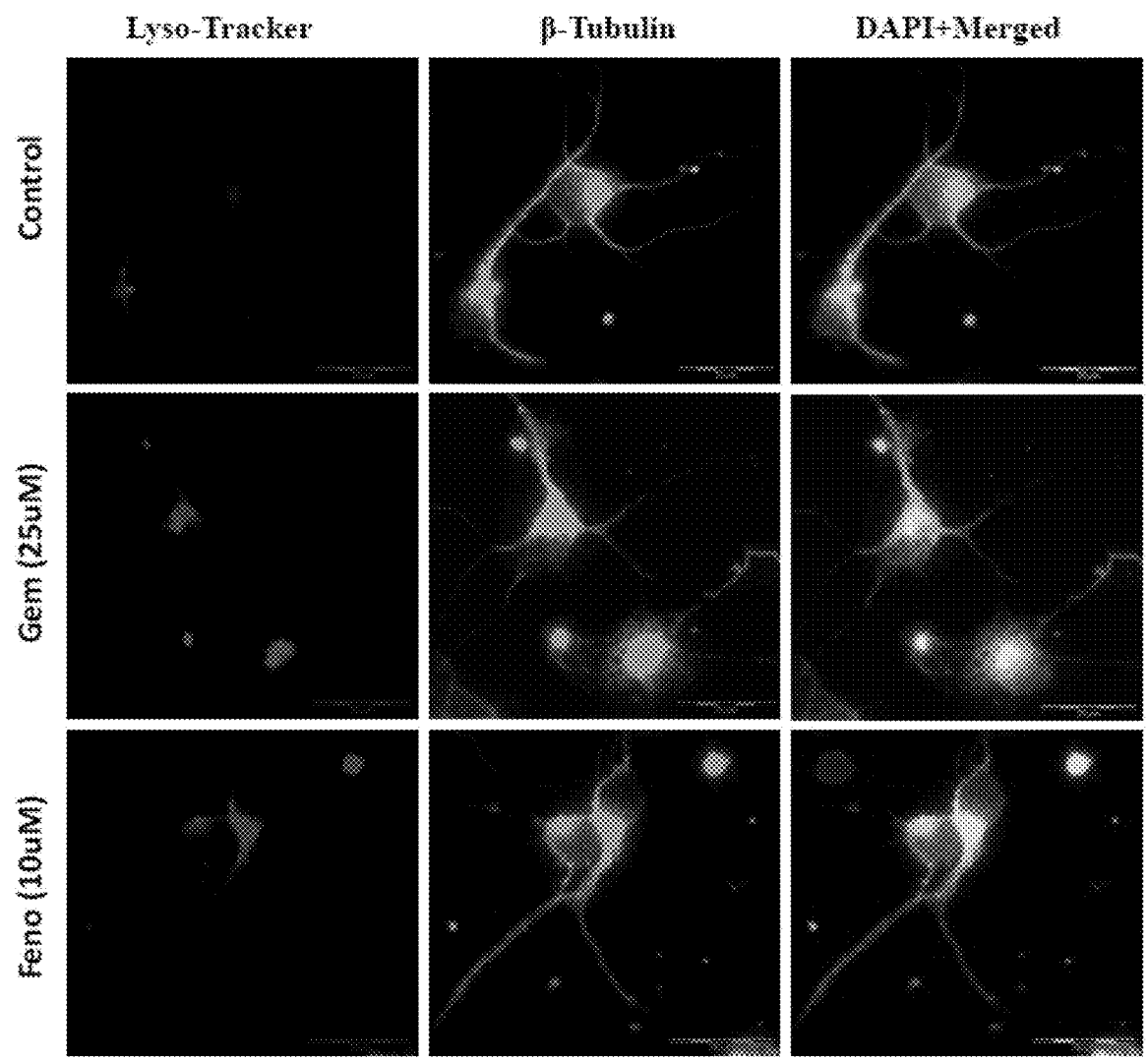
FIG. 10 shows the upregulation of lysosomal proliferation in primary human neurons by gemfibrozil and fenofibrate. Cells were treated with 25 μM gemfibrozil and 10 μM fenofibrate for 24 hours followed by labeling lysosomes with LysoTracker. DAPI was used to visualize nuclei. Results represent 3 independent experiments.
Figure 11:
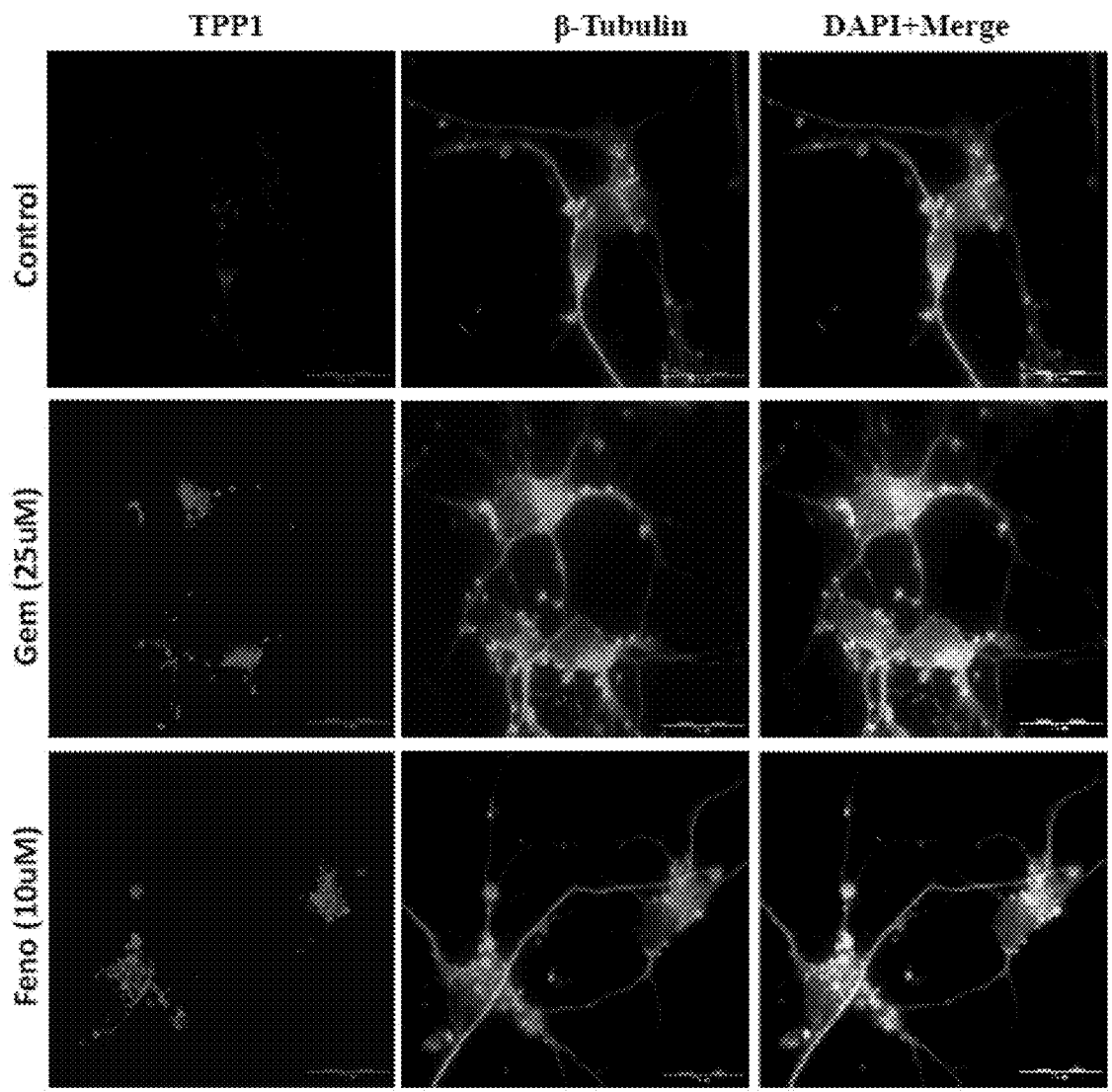
FIG. 11 shows the upregulation of the lysosomal marker protein tripeptidyl peptidase 1 (TPP1) by gemfibrozil and fenofibrate. Cells were treated with 25 μM gemfibrozil and 10 μM fenofibrate for 24 hours followed by double-labeling for TPP1 and β-tubulin (neuronal marker). DAPI was used to visualize nuclei. Results represent 3 independent experiments.
Figure 12:
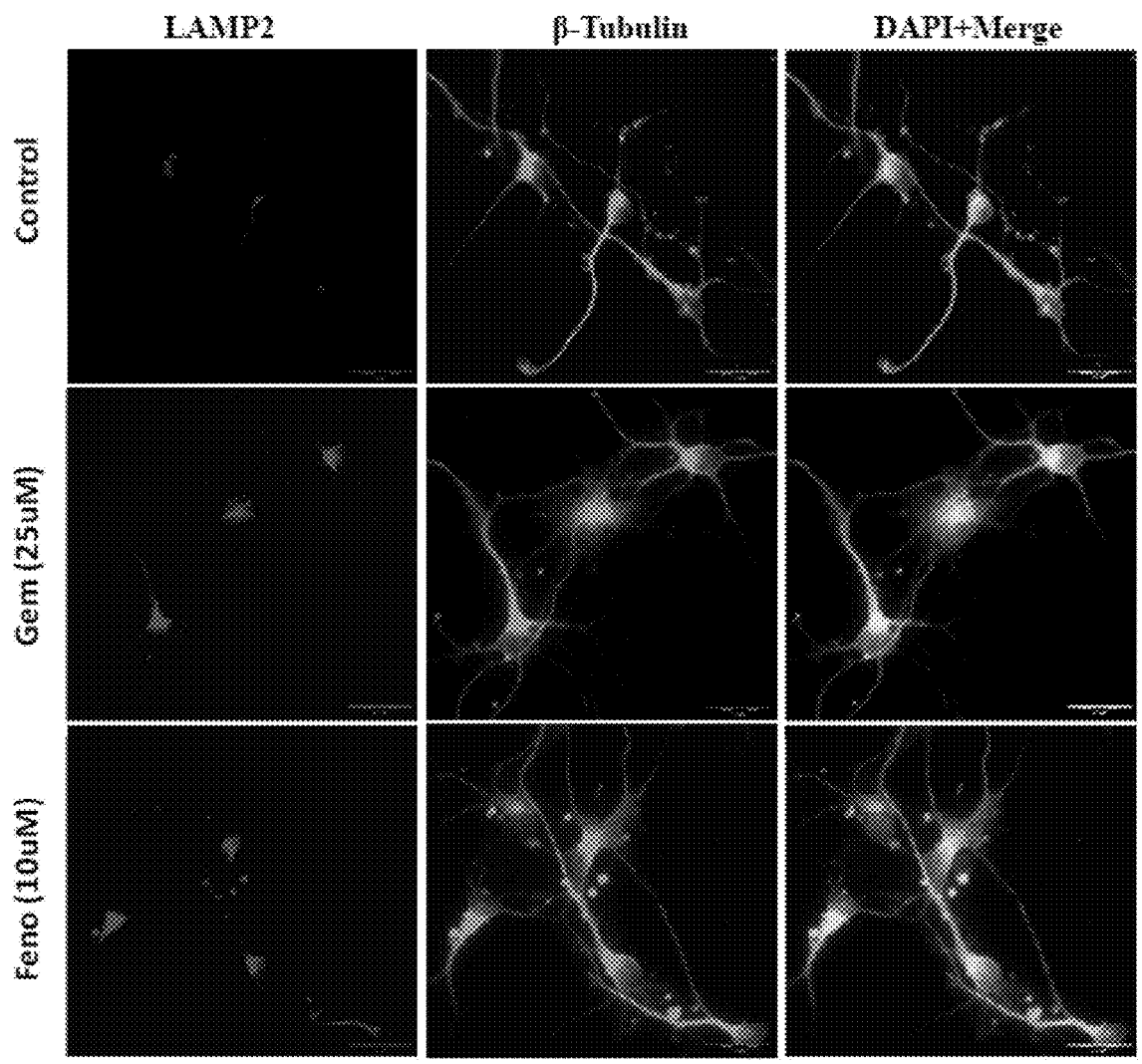
FIG. 12 shows the upregulation of lysosome-associated membrane protein 2 (LAMP2) in human neurons by gemfibrozil and fenofibrate. Cells were treated with 25 μM gemfibrozil and 10 μM fenofibrate for 24 hours followed by double-labeling for LAMP2 and β-tubulin (neuronal marker). DAPI was used to visualize nuclei. Results represent 3 independent experiments.
Figure 14:
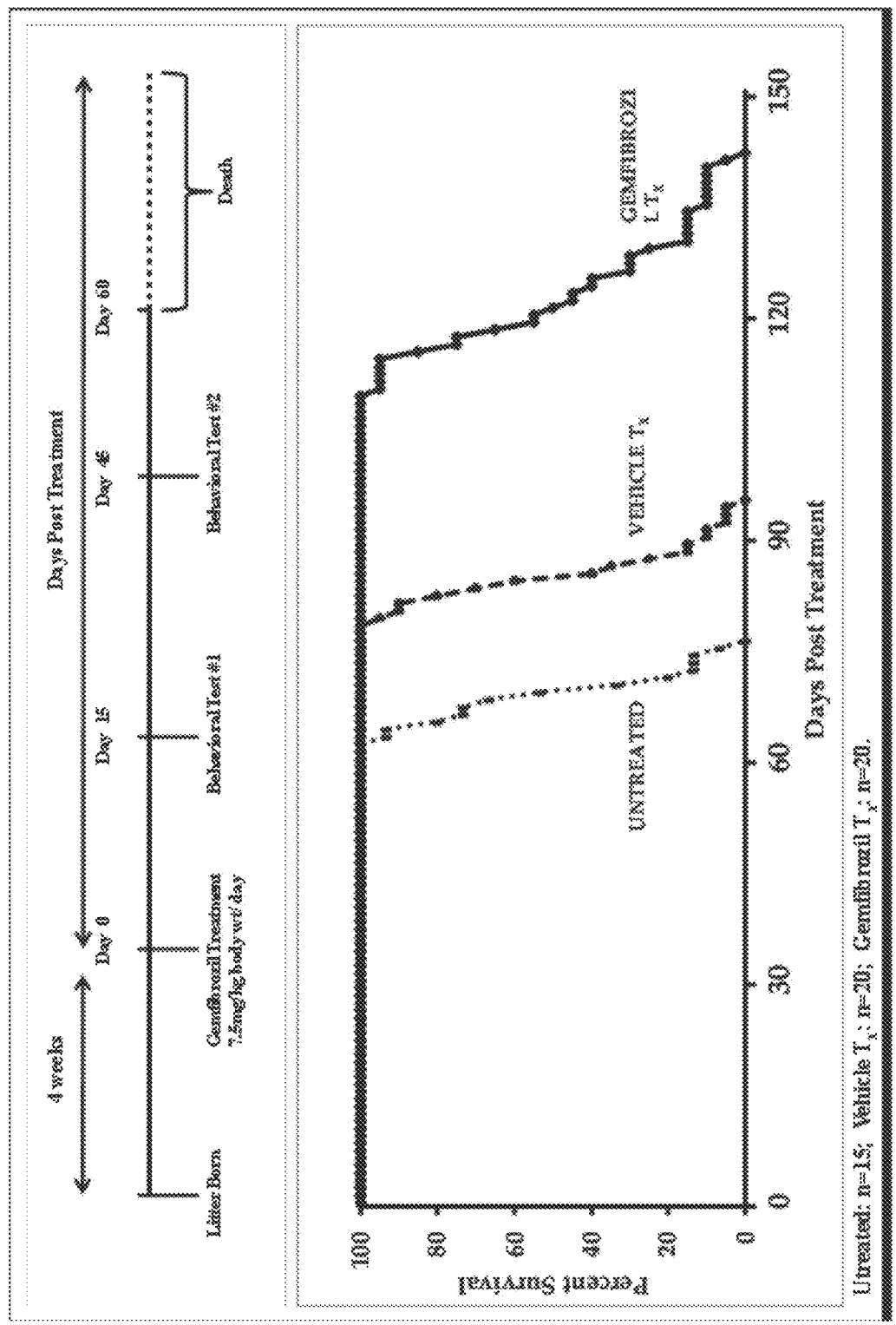
FIG. 14 illustrates that gemfibrozil prolongs the life span of CLN2 (−/−) mouse: CLN2(−/−) animals were orally administered with gemfibrozil dissolved in 0.1% methylcellulose at a dosage of 7.5 mg/kg body weight/day. Treatment was started from 4 weeks of age for all groups. Methyl cellulose was used as vehicle. Top panel: Schematic representation of experiments performed. Bottom panel: Kaplan-Meier plot for percentage survival of treated vs. vehicle or untreated animals.
Figure 15:
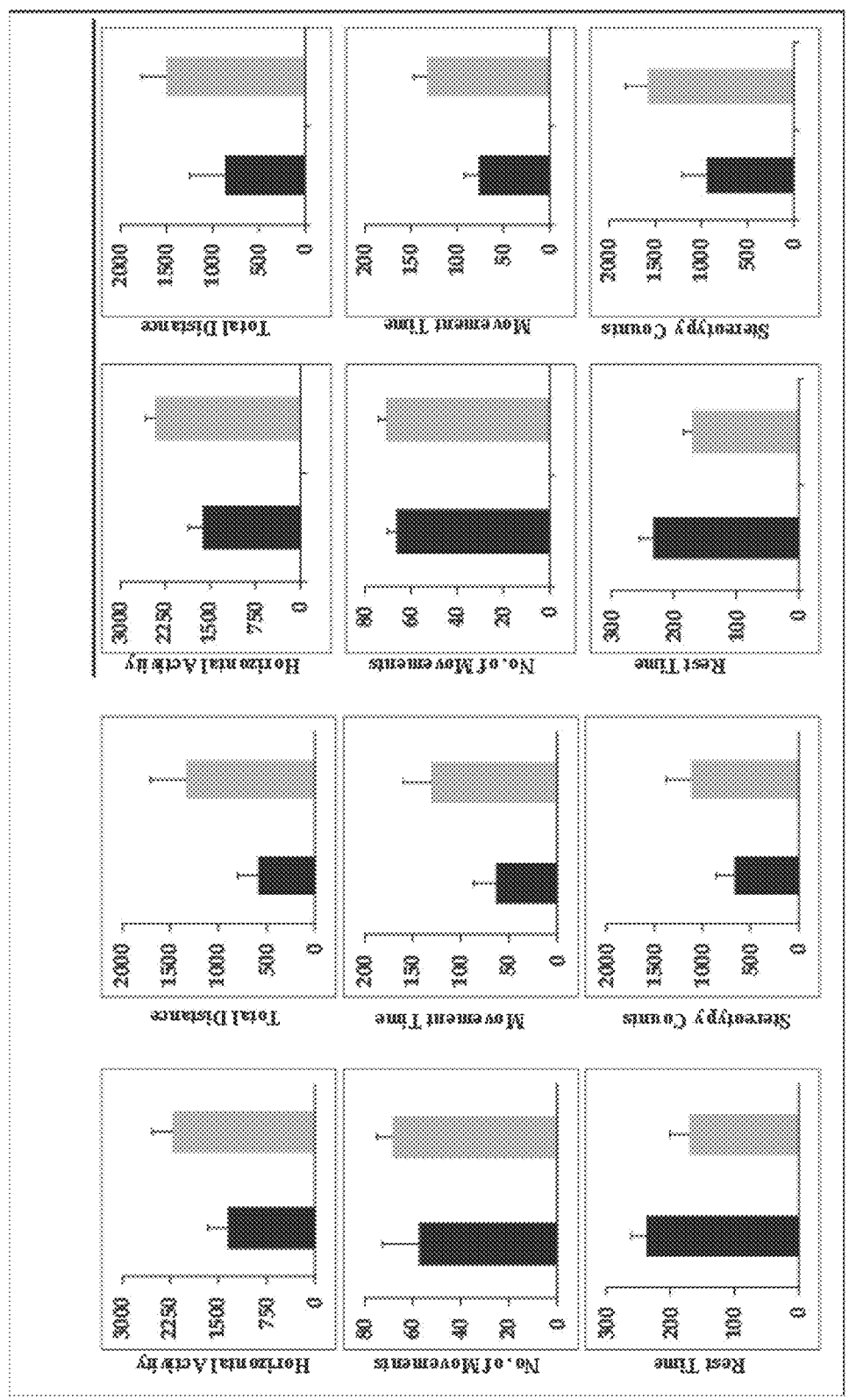
FIG. 15 illustrates that gemfibrozil treatment delays the loss of motor activity in CLN2 (−/−) mice: Treated and untreated CLN2 (−/−) animals from the previous experiment (FIG. 1) were monitored after 2 weeks (Left panel) and 6 weeks (right panel) of gemfibrozil treatment for various motor activity parameters. Each animal was allowed 5 mins of adaptation time followed by monitoring for 5 min. *p-value<0.05. n=15 (untreated), n=20 (treated)
Figure 16:
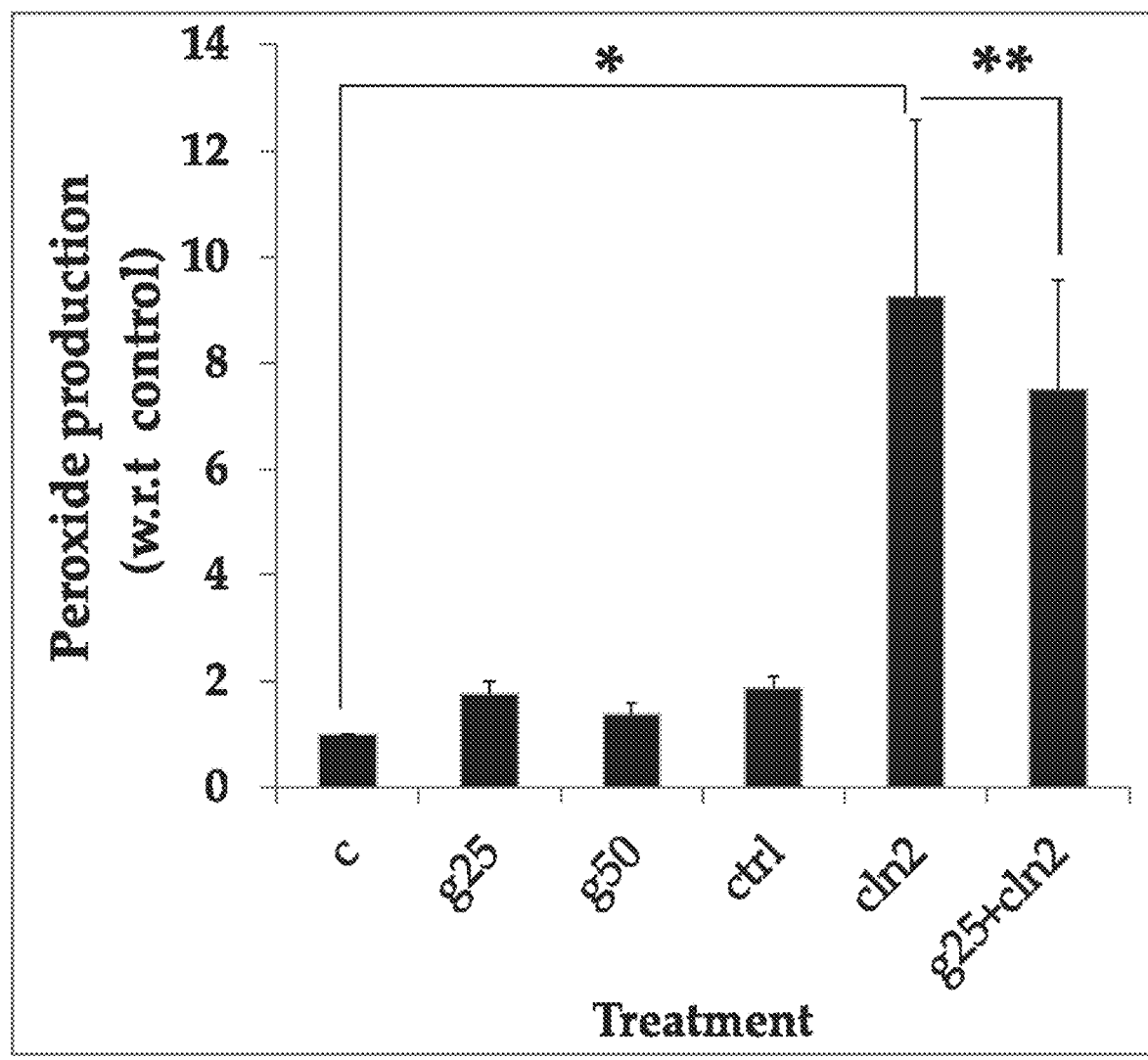
FIG. 16 illustrates that gemfibrozil treatment reduces peroxide production in CLN2 knockdown mouse astrocytes. Mouse astrocytes were transfected with CLN2 siRNA (1.0 μg) for 36 hrs and treated with gemfibrozil (25 μM) for 6 hrs. Cells were then harvested and subjected to peroxide assay. Results are mean±SD for three independent experiments. * & **p-value<0.05

After confirming the involvement of both PPARα and RXRα, we were interested to find out the actual role of the two factors. First, we examined whether there was any actual physical interaction between PPARα and RXRα. Mouse astrocytes were treated with gemfibrozil and RA separately as well as in combination and the nuclear extract was subjected to Co-IP for both PPARα and RXR. Immunoprecipitation with PPARα Ab showed increased presence of RXR in the immunoblot for the treated samples compared to control (FIG. 7A-i). Similarly, increased abundance of PPARα was also observed when the nuclear extracts were immunoprecipitated with RXR Ab (FIG. 7A-ii). These results demonstrate the presence of PPARα/RXRα heterodimer in the nucleus of cells stimulated with gemfibrozil and RA. These results are specific as we did not find any bands with IgG (FIG. 7A-iii). Levels of PPARα and RXRα and Histone3 (H3) have been shown as loading controls (FIG. 7A-iv). Next, we performed ChIP studies to show the recruitment of the PPARα and RXRα on the RXR binding site on the Cln2 gene (FIG. 7B). Chromatin fragments from cells treated with gemfibrozil and RA were immunoprecipitated with both PPARα Ab and RXRα Ab and the DNA obtained was amplified by PCR with primers spanning the RXR binding site on the Cln2 gene promoter. In both cases, we were able to amplify 200 bp fragments flanking the RXR binding site (FIG. 7C). In contrast, no amplification product was observed in any of the immunoprecipitates obtained with control IgG (FIG. 7C), suggesting the specificity of these interactions. These results suggest that gemfibrozil and RA are capable of recruiting both PPARα and RXRα to the RXR binding site of the Cln2 gene promoter (FIG. 7C).

Example 10

Summary of Examples 2-9

The classical late infantile neuronal ceroid lipofuscinosis (LINCLs) is an autosomal recessive disease, where the defective gene is Cln2, encoding tripeptidyl peptidase I (TPP1). At the molecular level LINCL is caused by accumulation of autofluorescent storage materials in neurons and other cell types. Currently there is no established treatment for this fatal disease. This study reveals a novel use of gemfibrozil and fenofibrate, FDA-approved lipid-lowering drugs, in upregulating TPP1 in brain cells. Both gemfibrozil and fenofibrate upregulated mRNA, protein and enzymatic activity of TPP1 in primary mouse neurons and astrocytes as well as human astrocytes and neuronal cells. Since gemfibrozil and fenofibrate are known to activate peroxisome proliferator-activated receptor-α (PPARα), the role of PPARα in gemfibrozil- and fenofibrate-mediated upregulation of TPP1 was investigated revealing that both drugs upregulated TPP1 mRNA, protein and enzymatic activity both in vitro and in vivo in wild type (WT) and PPARβ$^{-/-}$, but not PPARα–/–, mice. In an attempt to delineate the mechanism of TPP1 upregulation, it was found that the effects of the fibrate drugs were abrogated in the absence of retinoid X receptor-α (RXRα), a molecule known to form heterodimer with PPARα. Accordingly, all-trans retinoic acid, alone or together with gemfibrozil, upregulated TPP1. Co-immunoprecipitation and ChIP studies revealed the formation of PPARα-RXRα heterodimer and binding of the heterodimer to RXR binding site on the Cln2 promoter. Together, this study demonstrates a unique mechanism for the upregulation of TPP1 by fibrate drugs via PPARα: RXRα pathway.

Example 11

Discussion of Examples 2-9

The NCL family of disease can be considered to be one of the most important hereditary neurodegenerative lysosomal storage diseases (LSD) in children (34). Mutations in the Cln2 gene result in deficiency or loss of function of the TPP1 enzyme (9,30,35). There have been reports of over 68 missense mutations in the Cln2 gene including 35 single amino acid substitutions. Studies with 14 different naturally occurring disease associated mutations showed alteration of lysosomal transport, increased half-life of the proenzyme and improper folding, resulting to loss of function of the enzyme (9). Currently there is no established drug mediated therapy for LINCL, a classic subtype of the NCLs. Studies using adeno-associated virus (AAV) and other viral vectors expressing recombinant TPP1 demonstrate widespread expression of TPP1 and treatment of Cln2-targeted mice with these recombinant vectors shows slowing of disease associated pathology and increase in survival in mutant mice (36-38). However, levels of TPP1 activity achievable by AAV-mediated gene therapy can vary and depend on various critical parameters and there is considerable doubt whether similar effects can be achieved in humans (36,39)

On the other hand, restoration of activity at even low levels could prove helpful for most LSDs, where restoration of even <10% of normal activity may have therapeutic benefits (40). Studies with hypomorphs of Cln2 mutant mice, expressing different levels of TPP1 enzyme indicate that even 3% of normal TPP1 activity is capable of delaying the onset of the disease and 6% of the normal activity attenuates the disease and increases the lifespan of mice (40). Also two specific variants of mutated TPP1 were responsive to molecular chaperone treatment, indicating that folding improvement strategies can be used to restore the enzymatic activity (9). Recent studies suggest that some misfolded variants or misprocessed proteins may also be rescued by treatment in permissive temperatures under suitable condition (9). There have also been reports of some mutations in TPP1 (Arg447His), which apparently may not have any pathogenic effect (31). Moreover, a sensitive enzyme activity assay detected residual levels of TPP1 activity in various biological samples from patients who were confirmed to have LINCL by genetic analysis (30). This study also showed the presence of enzyme activity in various animals having NCL-like neurodegenerative symptoms rendering them unsuitable for being a model for classical LINCL (30). Furthermore, using highly sensitive capillary electrophoresis technique, Vigilio et al, reported that lymphocytes from patients affected with LINCL exhibited TPP1 activity, although at low levels (in a range between 0.1 and 0.8 mU/mg) (8). These findings about the presence of residual enzymatic activity in LINCL patients are very interesting as it indicate the presence of at least a few copies of the functional gene in the system. Therefore, identifying specific drugs and understanding the mechanisms by which these drugs can upregulate the endogenous normal copies of the gene may be a critical step for LINCL therapy.

Gemfibrozil, marketed as 'Lopid', and fenofibrate, known as 'Tricor', are FDA-approved drugs prescribed for hyperlipidemia (10,12). Here we delineate for the first time that, these drugs are capable of upregulating TPP1 in brain cells. This finding was confirmed by both mRNA and protein studies in both mouse and human cells. The increase in protein levels was throughout the brain as neurons isolated from different brain regions of mouse showed increased TPP1 expression upon treatment with gemfibrozil. In case of LINCL, the presence of functionally active TPP1 enzyme is critical for therapy, as we have to rely on the upregulation of residual enzyme activity in patients. The TPP1 activity assay, performed in different cell types, clearly showed that there was significant increase in the activity of the enzyme which is a result of increased levels of the protein. Considering the possibility of treatment by upregulation of the endogenous Cln2 gene, this finding could be of importance in the therapy of LINCL.

Over the last few years, a number of studies emphasized the role of PPARs in different regulatory and modulatory pathways. It is also well known that PPARα is activated by polyunsaturated fatty acids and oxidized derivatives and by lipid-modifying drugs of the fibrate family, including fenofibrate and gemfibrozil (41,42). PPARα is present in the cytoplasm as an inactive complex with heat-shock protein 90 (HSP-90) and hepatitis virus B-X-associated protein-2 (XAP-2), which act as an inhibitor of PPARα. Fibrate drugs replace the HSP90 repressor complex and help to rescue the transcriptional activity of PPARα (15). Therefore, we investigated the role of the PPAR group of receptors in this phenomenon. We examined all three PPARs, viz PPARα, PPARβ, PPARγ for their involvement in upregulation of TPP1. These studies clearly indicate the involvement of PPARα, but not PPARβ and PPARγ, in this process. In astrocytes from WT and PPARα$^{-/-}$ and PPARβ$^{-/-}$ mice, both the TPP1 mRNA and protein analysis showed the involvement of only PPARα. Involvement of PPARγ was ruled out as studies using known antagonist of PPARγ revealed no effect. TPP1 enzyme activity in the cell extracts was also increased in WT and PPARβ$^{-/-}$, but not PPARα$^{-/-}$, cells. The in vitro studies were further validated by in vivo studies, where we used the knockout mice for PPARα and PPARβ. Our in vivo results also supported the cell culture data.

In order to delineate the mechanism of fibrate drug-mediated upregulation of TPP1, we analyzed the promoter region of the Cln2 gene. Surprisingly, no PPAR binding site was found in the mouse Cln2 promoter, but further analysis of the promoter revealed a RXR binding site. It is well known that in order to bind to DNA and activate transcription, PPAR requires the formation of heterodimer with the retinoid X receptor (RXR) (43). Together the PPAR/RXR heterodimer regulates the transcription of genes for which products are involved in lipid homeostasis, cell growth, and differentiation (44,45). This led us to think whether the pathway of TPP1 upregulation requires a co-operative effect of both PPAR and RXR. It was observed that the activation of RXR by low doses of RA alone (0.5 μM) was capable of upregulating TPP1 to a comparable level of that of gemfibrozil (10 μM). Also, when cells were treated with both gemfibrozil and RA together, they co-operatively enhanced the expression of TPP1 by almost more than 3 fold compared to the levels achieved by either gemfibrozil or RA alone, which implies that a combinatorial therapy could be more useful than using the compounds separately for treatment. Furthermore, the effect of both gemfibrozil and RA were abrogated in the absence of either RXRα or PPARα. The Co-IP studies performed with the nuclear extracts on astrocytes stimulated with gemfibrozil and RA demonstrated physical interaction between PPARα and RXR. These data clearly suggest that the treatment with gemfibrozil and RA activates both PPARα and RXRα which forms heterodimer in the nucleus. The ChIP data indicated the recruitment of the PPARα and RXRα on the RXR binding site of the Cln2 promoter, hence validating our hypothesis. Collectively, these data outlines a unique mechanism where gemfibrozil, a known activator of PPARα, and RA, an agonist of RXRα, together can upregulate TPP1 in brain cells via PPARα/RXRα heterodimer.

Gemfibrozil and other fibrate drugs are known to reduce superoxide, lipid peroxidation products. It also strengthens the cellular defense by stimulating the activity of anti-oxidant proteins such as paraxonase and is associated with free radical scavenging ability as well as metal ion chelation. Therefore, apart from its lipid lowering effects, these drugs also have anti-inflammatory, immunomodulatory and anti-oxidative properties (14,27,46-48). In the NCL cases, predominantly in LINCL, different brain regions have been shown to be immunoreactive for 4-hydroxynonenal (4-HNE) or 8-hydroxydeoxyguanosine (8-OHdG), popular markers for evaluation of oxidative stress which may be caused due to accumulation of lipofuscines and elevated cytokine response (1). Therefore, treatment with these drugs will not only lead to the upregulation of endogenous normal TPP1 leading to clearance of lipofuscines but also can be beneficial for the peripheral immune system by downregulating the inflammatory pathways generated due to accumulation of lipofuscines.

In summary, we have delineated that gemfibrozil and fenofibrate, FDA-approved lipid-lowering drugs, upregulate TPP1 in cultured mouse and human brain cells and in vivo in mouse brain via PPARα/RXRα pathway. Although the in vitro situation of mouse and human brain cells in culture and its treatment with gemfibrozil and fenofibrate may not truly resemble the in vivo situation of the CNS of patients with late infantile neuronal ceroid lipofuscinosis (LINCLs), our results clearly identify these two drugs as possible therapeutic agents for LINCL that can be immediately taken to clinical trials for testing.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

4. REFERENCES

1. Hachiya, Y., Hayashi, M., Kumada, S., Uchiyama, A., Tsuchiya, K., and Kurata, K. (2006) *Acta Neuropathol* 111, 168-177
2. Lane, S. C., Jolly, R. D., Schmechel, D. E., Alroy, J., and Boustany, R. M. (1996) *J Neurochem* 67, 677-683
3. Mole, S. E., Williams, R. E., and Goebel, H. H. (2005) *Neurogenetics* 6, 107-126
4. Sleat, D. E., Donnelly, R. J., Lackland, H., Liu, C. G., Sohar, I., Pullarkat, R. K., and Lobel, P. (1997) *Science* 277, 1802-1805
5. Goebel, H. H. (1995) *J Child Neurol* 10, 424-437
6. Vines, D. J., and Warburton, M. J. (1999) *FEBS Lett* 443, 131-135
7. Chang, M., Cooper, J. D., Sleat, D. E., Cheng, S. H., Dodge, J. C., Passini, M. A., Lobel, P., and Davidson, B. L. (2008) *Mol Ther* 16, 649-656
8. Viglio, S., Marchi, E., Wisniewski, K., Casado, B., Cetta, G., and Iadarola, P. (2001) *Electrophoresis* 22, 2343-2350
9. Walus, M., Kida, E., and Golabek, A. A. *Hum Mutat* 31, 710-721
10. Robins, S. J., Collins, D., Wittes, J. T., Papademetriou, V., Deedwania, P. C., Schaefer, E. J., McNamara, J. R., Kashyap, M. L., Hershman, J. M., Wexler, L. F., and Rubins, H. B. (2001) *JAMA* 285, 1585-1591
11. Rubins, H. B., and Robins, S. J. (1992) *J Intern Med* 231, 421-426
12. Rubins, H. B., Robins, S. J., Collins, D., Fye, C. L., Anderson, J. W., Elam, M. B., Faas, F. H., Linares, E., Schaefer, E. J., Schectman, G., Wilt, T. J., and Wittes, J. (1999) *N Engl J Med* 341, 410-418
13. Dasgupta, S., Roy, A., Jana, M., Hartley, D. M., and Pahan, K. (2007) *Mol Pharmacol* 72, 934-946
14. Ghosh, A., and Pahan, K. *J Biol Chem* 287, 27189-27203
15. Pahan, K., Jana, M., Liu, X., Taylor, B. S., Wood, C., and Fischer, S. M. (2002) *J Biol Chem* 277, 45984-45991
16. Roy, A., and Pahan, K. (2009) *Immunopharmacol Immunotoxicol* 31, 339-351
17. Brahmachari, S., and Pahan, K. (2007) *J Immunol* 179, 275-283
18. Saha, R. N., and Pahan, K. (2007) *Free Radic Biol Med* 42, 1866-1878
19. Giulian, D., and Baker, T. J. (1986) *J Neurosci* 6, 2163-2178
20. Jana, A., and Pahan, K. *J Neurosci* 30, 12676-12689
21. Saha, R. N., Jana, M., and Pahan, K. (2007) *J Immunol* 179, 7101-7109
22. Jana, M., Jana, A., Pal, U., and Pahan, K. (2007) *Neurochem Res* 32, 2015-2022
23. Jana, M., and Pahan, K. (2005) *Free Radic Biol Med* 39, 823-831
24. Khasnavis, S., Jana, A., Roy, A., Wood, T., Ghosh, S., Watson, R., and Pahan, K. *J Biol Chem*
25. Khasnavis, S., and Pahan, K. *J Neuroimmune Pharmacol* 7, 424-435
26. Dasgupta, S., Jana, M., Zhou, Y., Fung, Y. K., Ghosh, S., and Pahan, K. (2004) *J Immunol* 173, 1344-1354
27. Corbett, G. T., Roy, A., and Pahan, K. *J Immunol* 189, 1002-1013
28. Saha, R. N., Liu, X., and Pahan, K. (2006) *J Neuroimmune Pharmacol* 1, 212-222
29. Nelson, J. D., Denisenko, O., and Bomsztyk, K. (2006) *Nat Protoc* 1, 179-185
30. Sohar, I., Sleat, D. E., Jadot, M., and Lobel, P. (1999) *J Neurochem* 73, 700-711
31. Sleat, D. E., Gin, R. M., Sohar, I., Wisniewski, K., Sklower-Brooks, S., Pullarkat, R. K., Palmer, D. N., Lerner, T. J., Boustany, R. M., Uldall, P., Siakotos, A. N., Donnelly, R. J., and Lobel, P. (1999) *Am J Hum Genet* 64, 1511-1523
32. Cullingford, T. E., Bhakoo, K., Peuchen, S., Dolphin, C. T., Patel, R., and Clark, J. B. (1998) *J Neurochem* 70, 1366-1375
33. Nishizawa, H., Manabe, N., Morita, M., Sugimoto, M., Imanishi, S., and Miyamoto, H. (2003) *J Reprod Dev* 49, 539-545
34. Hemsley, K. M., and Hopwood, J. J. *J Inherit Metab Dis* 33, 363-371
35. Bellettato, C. M., and Scarpa, M. *J Inherit Metab Dis* 33, 347-362
36. Vuillemenot, B. R., Katz, M. L., Coates, J. R., Kennedy, D., Tiger, P., Kanazono, S., Lobel, P., Sohar, I., Xu, S., Cahayag, R., Keve, S., Koren, E., Bunting, S., Tsuruda, L. S., and O'Neill, C. A. *Mol Genet Metab* 104, 325-337
37. Worgall, S., Sondhi, D., Hackett, N. R., Kosofsky, B., Kekatpure, M. V., Neyzi, N., Dyke, J. P., Ballon, D., Heier, L., Greenwald, B. M., Christos, P., Mazumdar, M., Souweidane, M. M., Kaplitt, M. G., and Crystal, R. G. (2008) *Hum Gene Ther* 19, 463-474

38. Xu, S., Wang, L., El-Banna, M., Sohar, I., Sleat, D. E., and Lobel, P. *Mol Ther* 19, 1842-1848
39. Cabrera-Salazar, M. A., Roskelley, E. M., Bu, J., Hodges, B. L., Yew, N., Dodge, J. C., Shihabuddin, L. S., Sohar, I., Sleat, D. E., Scheule, R. K., Davidson, B. L., Cheng, S. H., Lobel, P., and Passini, M. A. (2007) *Mol Ther* 15, 1782-1788
40. Sleat, D. E., El-Banna, M., Sohar, I., Kim, K. H., Dobrenis, K., Walkley, S. U., and Lobel, P. (2008) *Mol Genet Metab* 94, 222-233
41. Marx, N., Duez, H., Fruchart, J. C., and Staels, B. (2004) *Circ Res* 94, 1168-1178
42. Sands, M. S., and Davidson, B. L. (2006) *Mol Ther* 13, 839-849
43. Juge-Aubry, C. E., Gorla-Bajszczak, A., Pernin, A., Lemberger, T., Wahli, W., Burger, A. G., and Meier, C. A. (1995)*J Biol Chem* 270, 18117-18122
44. Marcus, S. L., Miyata, K. S., Rachubinski, R. A., and Capone, J. P. (1995) *Gene Expr* 4, 227-239
45. Krey, G., Mahfoudi, A., and Wahli, W. (1995)*Mol Endocrinol* 9, 219-231
46. Jackson, T. C., Mi, Z., Bastacky, S. I., McHale, T., Melhem, M. F., Sonalker, P. A., Tofovic, S. P., and Jackson, E. K. (2007) *Transpl Int* 20, 277-290
47. Xu, J., Racke, M. K., and Drew, P. D. (2007) *J Neurochem* 103, 1801-1810
48. Jana, M., Jana, A., Liu, X., Ghosh, S., and Pahan, K. (2007) *J Immunol* 179, 4142-4152

What is claimed is:

1. A method for treatment of a neurodegenerative disease, comprising administering to a subject in need of such treatment a composition comprising a therapeutically effective amount of an agent that mediates upregulation of TPP1, the agent comprising a lipid-lowering drug, wherein the neurodegenerative disease is a lysosomal storage disorder, and wherein the lipid-lowering drug is a fibrate, and wherein the lysosomal storage disease is Tay-Sach's disease.

2. The method of claim 1, wherein the fibrate is gemfibrozil or fenofibrate.

3. The method of claim 1, wherein TPP1 is upregulated by increasing TPP1 mRNA levels, increasing TPP1 protein levels, increasing TPP1 enzymatic activity, or activating a PPAR-RXR heterodimer.

4. A method for treatment of a neurodegenerative disease, comprising administering to a subject in need of such treatment a composition comprising a therapeutically effective amount of an agent that mediates upregulation of TPP1, the agent comprising a lipid-lowering drug, wherein the neurodegenerative disease is a lysosomal storage disorder, and wherein the lipid-lowering drug is a fibrate, wherein the composition further comprises a therapeutically effective amount of all-trans retinoic acid.

5. The method of claim 4, wherein administering all-trans retinoic acid and a fibrate provides a greater therapeutic effect in the subject than administration of all-trans retinoic acid or the fibrate alone.

6. A method for treatment of a neurodegenerative disease, comprising administering to a subject in need of such treatment a composition comprising a therapeutically effective amount of an agent, wherein the agent restores TPP1 activity, the agent comprising a lipid-lowering drug, wherein the neurodegenerative disease is a lysosomal storage disorder, and wherein the lipid-lowering drug is a fibrate, and wherein the lysosomal storage disease is Tay-Sach's disease.

7. The method of claim 6, wherein the fibrate is gemfibrozil or fenofibrate.

8. A method for treatment of a neurodegenerative disease, comprising administering to a subject in need of such treatment a composition comprising a therapeutically effective amount of an agent, wherein the agent restores TPP1 activity, the agent comprising a lipid-lowering drug, wherein the neurodegenerative disease is a lysosomal storage disorder, and wherein the lipid-lowering drug is a fibrate, wherein the therapeutically effective amount of the fibrate is lower when the fibrate is administered in combination with all-trans retinoic acid.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: ClnI Sense Primer

<400> SEQUENCE: 1
acacagagga ccgcctgggg                                                     20

<210> SEQ ID NO 2
<211> LENGTH: 20
<212> TYPE: DNA
<213> ORGANISM: Artificial Sequence
<220> FEATURE:
<223> OTHER INFORMATION: ClnI Antisense primer

<400> SEQUENCE: 2
tcatgcacgg cccacacagc                                                     20

<210> SEQ ID NO 3
<211> LENGTH: 22
<212> TYPE: DNA
<213> ORGANISM: Artificial Sequence
<220> FEATURE:
<223> OTHER INFORMATION: Cln2 Sense Primer

<400> SEQUENCE: 3
caccatccag ttacttcaat gc                                                  22

<210> SEQ ID NO 4
<211> LENGTH: 22
<212> TYPE: DNA
<213> ORGANISM: Artificial Sequence
<220> FEATURE:
<223> OTHER INFORMATION: Cln2 Antisense Primer

<400> SEQUENCE: 4
ctgaccctcc acttcttcat tc                                                  22

<210> SEQ ID NO 5
<211> LENGTH: 20
<212> TYPE: DNA
<213> ORGANISM: Artificial Sequence
<220> FEATURE:
<223> OTHER INFORMATION: Cln3 Sense Primer

<400> SEQUENCE: 5
tgctgccctg ccatcgagtg                                                     20
```

<210> SEQ ID NO 6
<211> LENGTH: 20
<212> TYPE: DNA
<213> ORGANISM: Artificial Sequence
<220> FEATURE:
<223> OTHER INFORMATION: Cln3 Antisense Primer

<400> SEQUENCE: 6
ggcagcgctc agcatcacca                                            20

<210> SEQ ID NO 7
<211> LENGTH: 20
<212> TYPE: DNA
<213> ORGANISM: Artificial Sequence
<220> FEATURE:
<223> OTHER INFORMATION: Gadph Sense Primer

<400> SEQUENCE: 7
gcacagtcaa ggccgagaat                                            20

<210> SEQ ID NO 8
<211> LENGTH: 20
<212> TYPE: DNA
<213> ORGANISM: Artificial Sequence
<220> FEATURE:
<223> OTHER INFORMATION: Gadph Antisense Primer

<400> SEQUENCE: 8
gccttctcca tggtggtgaa                                            20

<210> SEQ ID NO 9
<211> LENGTH: 20
<212> TYPE: DNA
<213> ORGANISM: Artificial Sequence
<220> FEATURE:
<223> OTHER INFORMATION: Cln2 promoter sense primer

<400> SEQUENCE: 9
cagctgccat gtcccccagc                                            20

<210> SEQ ID NO 10
<211> LENGTH: 21
<212> TYPE: DNA
<213> ORGANISM: Artificial Sequence
<220> FEATURE:
<223> OTHER INFORMATION: Cln2 promoter antisense primer

<400> SEQUENCE: 10
tgcgcagctc tgtgtcatcc g                                          21

<210> SEQ ID NO 11
<211> LENGTH: 21
<212> TYPE: DNA
<213> ORGANISM: Artificial Sequence
<220> FEATURE:
<223> OTHER INFORMATION: Cln2 promoter set 2 sense primer

<400> SEQUENCE: 11
gctccctctc ctcagctgcc a                                          21

<210> SEQ ID NO 12
<211> LENGTH: 20
<212> TYPE: DNA
<213> ORGANISM: Artificial Sequence
<220> FEATURE:

```
<223> OTHER INFORMATION: Cln2 promoter set 2 antisense primer

<400> SEQUENCE: 12
catccggagg ctccaggcca                                                  20
```